US006960694B2

(12) United States Patent
Barnicki et al.

(10) Patent No.: US 6,960,694 B2
(45) Date of Patent: Nov. 1, 2005

(54) PROCESSES FOR PREPARING β-HYDROXY-KETONES AND α,β-UNSATURATED KETONES

(75) Inventors: Scott Donald Barnicki, Kingsport, TN (US); Jennifer Ellen McCusker-Orth, Kingsport, TN (US); Jerry Lynn Miller, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/611,394

(22) Filed: Jul. 1, 2003

(65) Prior Publication Data

US 2005/0004401 A1 Jan. 6, 2005

(51) Int. Cl.⁷ .............................................. C07C 45/72
(52) U.S. Cl. ........................ 568/390; 568/392; 568/396
(58) Field of Search ................................ 568/390, 392, 568/396

(56) References Cited

U.S. PATENT DOCUMENTS

| | | | |
|---|---|---|---|
| 2,088,015 A | 7/1937 | Wickert | |
| 2,088,016 A | 7/1937 | Wickert | |
| 2,088,017 A | 7/1937 | Wickert et al. | |
| 2,088,018 A | 7/1937 | Wickert et al. | |
| 2,200,216 A | 5/1940 | Loewenberg et al. | |
| 2,499,172 A | 2/1950 | Smith | |
| 2,852,563 A | 9/1958 | Hagemeyer, Jr. et al. | |
| 3,248,428 A | 4/1966 | Porter, Jr. et al. | |
| 3,670,026 A | 6/1972 | Lamparsky et al. | |
| 4,049,571 A | 9/1977 | Nissen et al. | |
| 4,101,586 A | 7/1978 | Deem et al. | |
| 4,102,930 A | 7/1978 | Deem | |
| 4,146,581 A | 3/1979 | Nissen et al. | |
| 4,270,006 A | 5/1981 | Heilen et al. | |
| 4,701,562 A | 10/1987 | Olson | |
| 4,739,122 A | 4/1988 | Letts | |
| 4,956,505 A | 9/1990 | Mais et al. | |
| 5,055,621 A | 10/1991 | Payne | |
| 5,243,081 A | 9/1993 | Ishino et al. | |
| 5,300,654 A | 4/1994 | Nakajima et al. | |
| 5,434,313 A | 7/1995 | Harrison et al. | |
| 5,583,263 A | 12/1996 | Muthusamy et al. | |
| 5,663,452 A | 9/1997 | Kulmala et al. | |
| 5,840,992 A | 11/1998 | Kido et al. | |
| 5,936,131 A | 8/1999 | Teissier et al. | |
| 6,232,506 B1 | 5/2001 | Kido et al. | |
| 6,271,171 B1 | 8/2001 | Teissier et al. | |
| 6,288,288 B1 | 9/2001 | Springer | |
| 6,433,230 B1 | 8/2002 | Bueschken et al. | |
| 6,583,323 B2 | 6/2003 | Krill | |
| 6,603,047 B2 | 8/2003 | Wiese et al. | |
| 2002/0058846 A1 | 5/2002 | Krill et al. | |
| 2002/0128517 A1 | 9/2002 | Krill | |
| 2002/0161264 A1 | 10/2002 | Wiese et al. | |
| 2002/0169347 A1 | 11/2002 | Kaizik et al. | |

FOREIGN PATENT DOCUMENTS

| | | |
|---|---|---|
| EP | 0 141 569 A2 | 5/1985 |
| GB | 446026 | 4/1936 |
| GB | 549006 | 11/1942 |
| GB | 1010695 | 11/1965 |
| WO | WO 02/24621 A1 | 3/2002 |

OTHER PUBLICATIONS

U.S. Appl. No. 10/877,339, filed Aug. 25, 2004, Barnicki et al.
U.S. Appl. No. 10/713,727, filed Nov. 14, 2003, McCusker et al.
Periodic Table of Elements, as published in "Chemical and Engineering News", 63(5), 27, 1985.
Kyrides, Journal of the Amer. Chem. Soc., vol. 55, Aug., 1933, pp. 3431–3435.
Powell, Journal of the Amer. Chem. Soc., vol. 46, 1924, pp. 2514–2517.
Streitwieser and Heathcock, "Introduction to Organic Chemistry", 2nd Ed., 1981, pp. 392–396.
H. O. House, Modern Synthetic Reactions, 2nd Ed., 1972, pp. 595–599, 629–640.
Grignared and Dubien, Ann. Chim., vol. 2, 1924, pp. 282–290.
T. A. Geissman, Chapter 3, Organic Reactions, vol. 2, R. Adams, editor, 1944, pp. 94–113.
Weizmann and Garrard, J. Chem. Soc., Pt. 1, vol. 117, 1920, pp. 324–338.
Eccott and Linstead, J. Chem. Soc., Pt. 1, vol. 133, 1930, pp. 904–911.
Weizmann and Garrard, "Some Condensations of N–butyl Alcohol and N–butaldehyde", *J. Chem. Soc. Trans.*, vol. 117, 1920, pp. 324–338.
M. Lakshmi Kantam et al, "Aldol and Knoevenagel condensations catalysed by modified Mg–Al hydrotalcite:a solid base as catalyst useful in synthetic organic chemistry" *Chem. Comm.*, 1998, pp. 1033–1034.
PCT International Search Report and Written Opinion for PCT/US2004/020489.

*Primary Examiner*—Samuel Barts
*Assistant Examiner*—Sikarl A. Witherspoon
(74) *Attorney, Agent, or Firm*—Polly C. Owen; Bernard J. Graves, Jr.

(57) ABSTRACT

Processes for producing β-hydroxy-ketones and α,β-unsaturated ketones are disclosed which comprise the crossed condensation of an aldehyde with a ketone in the presence of a hydroxide or alkoxide of alkali metal or an alkaline earth metal as catalyst. The products of the process, β-hydroxy-ketones and α,β-unsaturated ketones, are useful for the preparation of many commercially important products in the chemical process industries including solvents, drug intermediates, flavors and fragrances, other specialty chemical intermediates.

92 Claims, No Drawings

PROCESSES FOR PREPARING β-HYDROXY-KETONES AND α,β-UNSATURATED KETONES

FIELD OF THE INVENTION

The invention relates to the field of ketone chemistry, and more specifically, to processes for producing β-hydroxy ketones and α,β-unsaturated ketones having improved yield and specificity.

BACKGROUND OF THE INVENTION

In an aldol condensation reaction, an aldehyde or ketone, with a hydrogen atom alpha to the carbonyl, react together to form a β-hydroxy-aldehyde or a β-hydroxy-ketone. The β-hydroxy-aldehyde or β-hydroxy-ketone can dehydrate in the presence of either an acid or a base to give a conjugated α,β-unsaturated aldehyde or ketone. The conditions needed for the aldol dehydration are often only slightly more vigorous than the conditions needed for the aldol condensation itself. As a result, the product of such aldol reactions often comprises both the β-hydroxy aldehyde or ketone and the α,β-unsaturated aldehyde or ketone.

Many methods are known in the art for dehydrating β-hydroxy-aldehydes or β-hydroxy-ketones to α,β-unsaturated aldehydes or ketones in fair to excellent yields. These include simple heating; acid-catalyzed dehydration using mineral acids or solid acid catalysts, with or without azeotropic removal of the water of reaction, as exemplified in U.S. Pat. No. 5,583,263, U.S. Pat. No. 5,840,992, U.S. Pat. No. 5,300,654, and Kyrides, JACS, Vol 55, August, 1933, pp. 3431–3435; heating with iodine crystals as in Powell, JACS, Vol.46, 1924, pp. 2514–17; and base-catalyzed dehydration as taught in Streitwieser and Heathcock, "Introduction to Organic Chemistry", $2^{nd}$ Ed., 1981, pp. 392–396.

In some cases, it is desirable to selectively hydrogenate the carbon-carbon double bond of the α,β-unsaturated aldehyde or ketone to give a saturated aldehyde or ketone. Many catalysts and methods are known for such hydrogenation reactions, as exemplified in U.S. Pat. Nos. 5,583,263 and 5,840,992, and U.S. Pat. Publ. Nos., 2002/0128517, 2002/058846, and 2002/0169347. Commercially important products of this type include methyl isobutyl ketone, made by the self-condensation of acetone; and methyl amyl ketone, methyl isoamyl ketone, and methyl propyl ketone, made by the crossed condensation of acetone with n-butyraldehyde, isobutyraldehyde, and acetaldehyde, respectively.

In other cases it is desirable to hydrogenate the carbon-carbon double bond of the α,β-unsaturated aldehyde or ketone, as well as the carbonyl group, to give a saturated alcohol. Many catalysts and methods are known for such hydrogenation reactions, as exemplified in U.S. Pat. Nos. 2,088,015, 2,088,016, 2,088,017, and 2,088,018. Such alcohols are useful in the production of surfactants and esters.

Aldehydes are more reactive, in general, than are ketones in base-catalyzed aldol condensations because of the greater ease of enolate ion formation of an aldehyde. As such, in a crossed condensation of a ketone with an aldehyde to produce a desired β-hydroxyketone, the self-condensation of the aldehyde is expected to occur in substantial quantities to produce an undesired β-hydroxyaldehyde by-product. Further, unhindered aldehydes, i.e., straight-chain aldehydes such as acetaldehyde, propionaldehyde, n-butyraldehyde, and n-pentanal, are more reactive toward self-condensation than hindered aldehydes, i.e., branched aldehydes such as 2-methyl-propanal and 3-methyl-butanal.

It is understood that the rate-limiting step in these reactions is often enolate ion formation, and that condensation and the subsequent dehydration reaction occur in rapid succession. These α-β unsaturated ketones and aldehydes are known to those skilled in the art to be quite reactive and susceptible to further consecutive, non-selective condensation, cyclization, and Michael-type addition reactions with the starting ketones and aldehydes, as well as themselves and other ketonic and aldehydic by-products. See, for example, H.O. House, Modern Synthetic Reactions, $2^{nd}$. Ed., 1972 pp. 595–599, 629–640.

Thus, without being bound by any theory, in the base-catalyzed condensation of an aldehyde of Formula 1, possessing at least one hydrogen atom alpha to the carbonyl, with a ketone of Formula II, to form a desired β-hydroxy-ketone or α-β unsaturated ketone of Formulae III or IV, three parallel reaction pathways are known to compete:

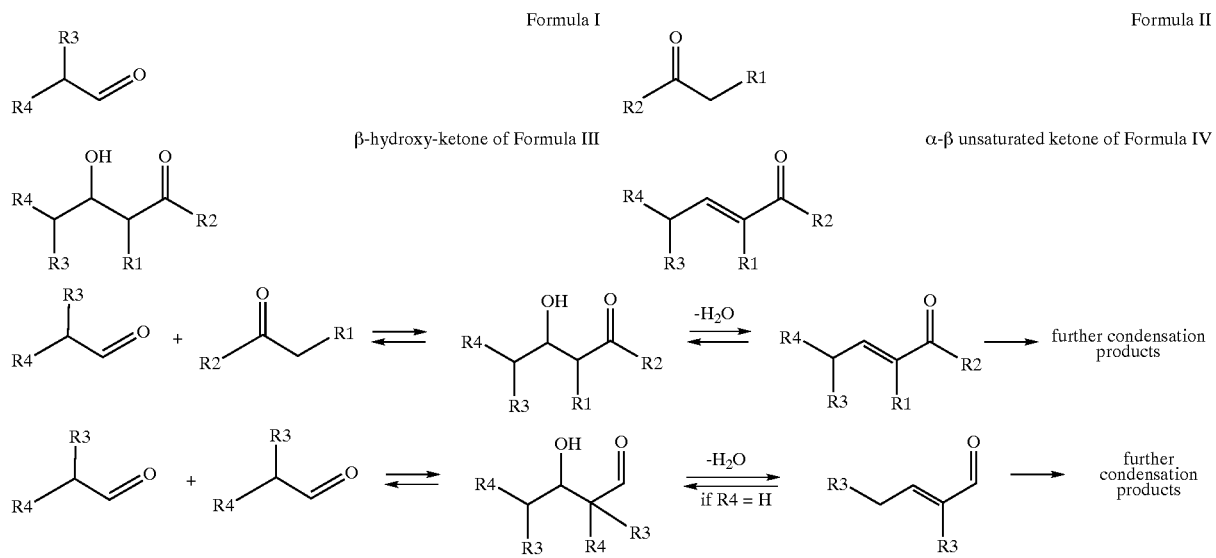

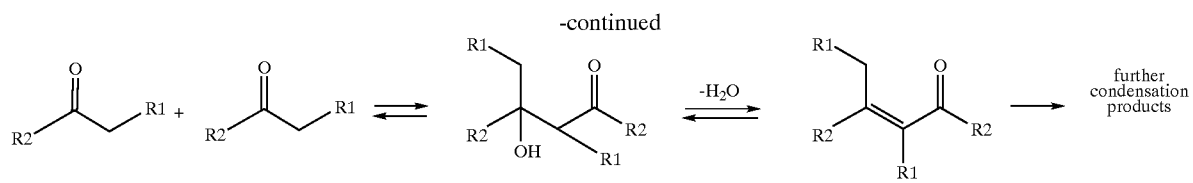

In general, R2 represents a C1 to C10 organic radical and R1, R3, and R4 represent hydrogen or a C1 to C10 organic radical.

R1 may represent a hydrogen, or else R1 and R2 may form members of a common cycloalkyl or aromatic ring, either of which may be substituted with one or more functional groups, or else R2 represents an alkyl group, which may be straight or branched, and which may be substituted with one or more functional groups;

R3 and R4 each independently represent hydrogen, or else R3 and R4 form members of a common cycloalkyl or aromatic ring, either of which may be substituted with one or more functional groups, or else one or both may represent a branched or unbranched, saturated or unsaturated aliphatic or alkyl-substituted cycloalkyl hydrocarbon radical; or else each represents an aryl hydrocarbon radical, or an alkylaryl hydrocarbon radical, either of which may be substituted with one or more functional groups.

One skilled in the art would expect a broad range of products from these reactions, and difficulty in stopping the reactions at the β-hydroxy-ketone stage. The further condensation of the α-β unsaturated ketones with the ketone of Formula II, or with the aldehyde of Formula I, or with other ketonic and aldehydic species, leads to a plethora of by-products and can represent significant yield losses as well as necessitating complicated and expensive purification schemes for the commercial production of high purity β-hydroxy-ketones and/or α,β-unsaturated ketones. For example, in the preparation of 2-heptanone via the condensation of n-butyraldehyde with acetone, the self-condensation of n-butyraldehyde to form 2-ethyl-2-hexenal is a particularly troublesome by-product. Its hydrogenated form; 2-ethylhexanal, boils less than 10° C. apart from 2-heptanone, and is therefore difficult to separate economically from 2-heptanone by distillation.

Generally, the equilibrium constant for ketone-ketone self-condensation is small, and products from this pathway are of lesser importance. One particular exception is when the ketone is acetone. Formation of the self-condensation products 4-hydroxy-4-methyl-2-pentanone and 4-methyl-3-penten-2-one can be appreciable under certain reaction conditions.

When the aldehyde of Formula I possesses no hydrogen alpha to the carbonyl, then the aldehyde-aldehyde self-condensation pathway cannot occur. However, under strongly basic conditions, the Cannizzaro reaction (in which two aldehyde groups are transformed into the corresponding alcohol and carboxylic acid salt) is known to be favorable and can represent significant yield losses of aldehyde, as well as consume a stoichiometric amount of base. T. A. Geissman, in Chapter 3 of Organic Reactions, Vol. 2, R. Adams, editor, 1944, pp 94–113, teaches a commonly employed procedure in which the aldehyde is shaken or stirred with strong (i.e., 50 weight percent) aqueous or alcoholic alkali metal hydroxides or alkoxides to effect the Cannizzaro reaction in good to excellent yields. Thus, one skilled in the art would expect the Cannizzaro reaction to occur, with consumption of the small amounts of base and subsequent termination of the reaction, using the process disclosed in the instant invention, as further discussed below.

Many methods have been disclosed in the art to perform crossed aldol condensation reactions. Such methods can be divided roughly into four general categories: 1) two-phase liquid reactions using dilute aqueous base as the catalyst, generally a hydroxide of an alkali- or alkali-earth metal; 2) base-catalyzed liquid phase reactions (may or may not be multiple liquid phases) with a compatibilizing agent, a solubilizing agent, or a phase transfer agent present (hereinafter sometimes referred to as a solubilizing agent), for example, an alkanol, a polyol, or a polyether alcohol, generally catalyzed by an alkoxide or hydroxide of an alkali- or alkali-earth metal; 3) amine-catalyzed condensation reactions; and 4) heterogeneous catalysis with a metal or metal oxide on a solid support. The latter method is often done in the gas phase, and the catalyst may combine further reaction functionality, i.e., hydrogenation.

The category comprising two-phase liquid reactions using dilute aqueous base as the catalyst, in the absence of a solubilizing agent, is exemplified in the following.

U.S. Pat. No. 6,232,506 discloses a process for producing 6-methyl-3-hepten-2-one, and its analogues, by the crossed aldol condensation of acetone with 3-methyl-butanal (isovaleraldehyde), catalyzed by an alkali metal or alkali earth metal hydroxide as catalyst. The catalyst is provided as a 0.5 to 30 weight percent, preferably 1 to 10 weight percent, aqueous solution, at a caustic-aldehyde molar ratio of 0.001 to 0.2. The process is carried out in semi-batch mode, with separate continuous feeds of aldehyde and dilute caustic to a stirred reaction zone initially comprising acetone. In Example 1 of the patent, using the preferred 2 wt. % aqueous caustic catalyst solution, the reaction mixture forms distinct aqueous and organic phases, with water being present in an amount of about 39 wt. %, based on the total weight of the reactant mixture Cited yields are typically about 66% to 6-methyl-3-hepten-2-one and 3.3% 6-methyl-4-hydroxy-heptan-2-one.

U.S. Pat. No. 5,840,992 ('992) teaches a process for producing 6-methylheptan-2-one by the crossed condensation of acetone with 3-methyl-butanal, in the presence of an aqueous alkali or alkali earth metal hydroxide as catalyst, at a catalyst-aldehyde molar ratio of 0.001 to 0.20. The resulting β-hydroxy ketone condensation product is further subjected to reduction under dehydrating conditions to produce 6-methylheptan-2-one. The process according to the '992 patent may be carried out continuously in plug flow or batch-wise mode. Typical molar selectivities on 3-methyl-butanal are about 75 to 80 percent, with the best results being achieved in the batch mode of operation. Although the '992 patent discloses that the basic catalyst substance may be used as an aqueous solution at a concentration between 1 and 50 percent, the process is reduced to practice only with a catalyst concentration of 5 weight percent aqueous sodium or potassium hydroxide. The authors of the '992 patent clearly fail to contemplate the advantages of using concentrated hydroxides or alkoxides of alkali earth- or alkali-metals as catalysts, for example at greater than 15 or 20 weight percent, while controlling the absolute amount of water present in the reaction mixture, as exemplified in the instant invention. Thus, the process disclosed in the '992 patent achieves only modest yields.

U.S. Pat. Publ. No. 2002/0161264 (the '264 publication) discloses a process for the preparation of α,β-unsaturated ketones by the crossed condensation of an aldehyde with a ketone. The condensation reaction described can be carried out in a tubular reactor as a multiphase liquid reaction in which a dilute aqueous caustic catalyst (0.1 to 15 weight percent caustic, preferably 0.1 to 5 weight percent) is the continuous phase and the aldehyde/ketone reactants are the dispersed phase. The disclosure of the '264 document explains that the reaction must be conducted with separate catalyst and reactant phases, and that the mass ratio of the aqueous caustic phase to the organic reactant phase can be from 2:1 to 10:1, preferably even greater. The reference clearly fails to contemplate the advantages of a high caustic catalyst phase reaction in which the amount of water present is kept relatively low.

U.S. Pat. No. 6,433,230 (the '230 patent) discloses a process similar to that described in the '264 publication, being a base-catalyzed aldol condensation that includes reacting the aldehydes and/or ketones with an aqueous catalyst solution under adiabatic reaction conditions, and thereafter separating the resulting reaction mixture. The condensation can be carried out in at least one stirred vessel or at least one tubular reactor, in which a dilute aqueous caustic catalyst (0.1 to 10 weight percent caustic, preferably 0.1 to 3 weight percent) constitutes one phase and the aldehyde/ketone reactants constitute another phase. Weight ratios of the organic reactant phase to the aqueous caustic phase of from 1:2 to 1:10, or preferably greater, are said to be useful. A cited advantage of the process is that, because of the adiabatic reaction conditions, the heat of reaction remains in the reaction mixture, assisting the subsequent rapid distillation of the top product, water and unreacted starting material. However, the reference clearly fails to contemplate the advantages of a high caustic catalyst phase reaction in which the amount of water present is kept relatively low.

A process similar to that disclosed in the '264 publication is disclosed in U.S. Pat. Publ. No.2002/0128517, a process for the preparation of 6-methylheptan-2-one and corresponding homologous β-branched methylketones, in particular phytone and trathydrogeranyl acetone, by the two-liquid phase crossed condensation of acetone with 3-methyl-butanal, prenal or the like, in the presence of both a dilute aqueous alkali or alkali earth metal hydroxide catalyst for the aldol step and a noble metal catalyst for hydrogenation. A base concentration of 0.01 to 20 weight percent in the aqueous catalyst phase is said to be useful, from 0.5 to 5 wt. % being preferred, though the concentration is said not to be critical. The processes exemplified in this document use relatively low concentrations of caustic with a relatively high amount of water, with respect to the total weight of the reactants. The reactivity toward self-condensation of the hindered, branched aldehyde, 3-methyl-butanal, is low, resulting in molar selectivities based on the aldehyde around 93–95 mole percent.

Kyrides, Journal of the Amer. Chem. Soc., Vol. 55, August, 1933, pp. 3431–3435, teaches a process for the crossed condensation of acetaldehyde or n-butanal with 2-butanone to produce the corresponding β-hydroxy ketone. The aldehyde is added semi-batchwise to a stirred reaction zone containing an excess of ketone and a small amount of 10 weight percent aqueous sodium hydroxide as catalyst. Typical conditions cited are temperatures less than 20° C. in the reaction zone, more typically less than 10° C., with a molar ratio of ketone to aldehyde between 7 and 8, and molar ratio of caustic to aldehyde between 0.0085 to 0.03. At these low temperatures, the solubility of the caustic in the reaction mixture is quite low and tends to separate into a distinct catalyst-containing liquid phase. The disclosed processes are characterized by long batch reaction times and poor space-time yields, and would require expensive refrigeration on a commercial scale to maintain temperatures less than 20° C. in the reaction zone. The processes give only modest molar yields on the aldehyde to the β-hydroxy ketones of about 70–85%.

Grignared and Dubien, Ann. Chim., Vol. 2, 1924, pp.282–290, teach a process for the crossed condensation of acetone with n-butyraldehyde to produce 4-hydroxy-2-heptanone. The aldehyde is added semi-batchwise to a stirred reaction zone containing an excess of ketone and a large amount of 12–15 weight percent aqueous sodium hydroxide as catalyst. Conditions cited are temperatures less than 20° C. in the reaction zone, preferably between 15° and 20° C., with a molar ratio of acetone to n-butyraldehyde of 2.5, and molar ratio of caustic to aldehyde of 0.31. Although the caustic concentration used is moderate, the amount of water thereby introduced, with respect to the total weight of reactants, is relatively high, so that the process is less advantageous than that according to the present invention. Further, at the low temperatures cited, the solubility of the caustic in the reaction mixture is quite low and tends to separate into a distinct catalyst-containing liquid phase. The process as disclosed requires long batch reaction times (six hours), provides poor space-time yields, would require expensive refrigeration on a commercial scale to maintain temperatures less than 20° C. in the reaction zone, and gives only modest molar yields on the aldehyde to the β-hydroxy ketone of about 80%.

U.S. Pat. No. 2,200,216 teaches a two stage batch reaction process for the production of high-molecular weight unsaturated ketones. The first step involves a crossed condensation of aldehydes containing from 4 to 8 carbon atoms with ketones containing from 3 to 5 carbon atoms in the presence of an alkaline earth hydroxide (15 weight percent aqueous barium hydroxide) to produce unsaturated ketones. After isolation, the unsaturated ketone products are then subjected to a second self-aldol reaction step in the presence of dilute alkali alkoxide in the corresponding alcohol. The concentration of alkaline earth hydroxide used is moderate, the amount of water thereby introduced into the reaction mixture (with respect to the total weight of the reactants) being relatively high. The disclosed multi-step process is fairly complicated, requires expensive reagents, and gives modest yields, typically about 70 percent per step.

U.S. Pat. No. 6,288,288 to Springer discloses a process for preparing saturated alcohols comprising effecting an aldol condensation of alkyl methyl ketones of 6 to 8 carbon atoms which are branched at the β-carbon atom, with aldehydes of 4 to 15 carbon atoms which are branched at the α-carbon atom, to form α,β-unsaturated ketones, with subsequent hydrogenation of the α,β-unsaturated ketones to obtain alcohols, wherein the aldol condensation is carried out at a temperature of 60 to 130° C. in the presence of a 30–55 weight percent aqueous solution of an alkali metal hydroxide.

Only the aldol condensations of 4-methyl-2-pentanone with 2-ethylhexanal and 4-methyl-2-pentanone with 2-methyl-butanal are disclosed in this document. The preferred caustic to aldehyde molar ratio is said to be from 0.15 to 1.0, with the best yields (typically 73 to 84 mole percent) achieved above a ratio of 0.35. Thus, very large amounts of caustic are required. Such a high caustic loading is not miscible in the organic reactants, and as a result, the process operates with two distinct liquid phases present in the reaction zone, as confirmed by the teaching that the aqueous catalyst phase can be decanted away from the organic product phase at the end of the reaction. In the preferred embodiment of this patent, the reactants are added slowly over several hours to a batch reaction zone, and the water generated by the dehydration of the initially formed β-hydroxy ketone is removed continuously. Although the concentration of the aqueous solution of an alkali metal hydroxide used is relatively high, the disclosed processes also use a relatively high amount of water, with respect to the total weight of the reactant mixtures. The process disclosed thus requires excessive levels of concentrated caustic catalyst, demonstrates poor reactor productivity, modest selectivity, and requires complicated water removal during the reaction.

A number of patents and references in the open literature are directed toward base-catalyzed, liquid phase aldol condensation reactions with a compatibilizing agent, a solubilizing agent, or a phase transfer agent present. U.S. Pat. Nos. 2,088,015 ('015), 2,0880,016 ('016), 2,0880,017 ('017), and 2,088,018 ('018) disclose related processes for the preparation of higher ketones in which the reactions are conducted in the presence of dilute alkali metal alkoxides in large amounts of the corresponding alcohol as solubilizing agent, typically 5–10 weight percent alkali metal hydroxide or alkoxide in methanol. Disclosed ketones include undecyl ketones ('015), nondecyl ketones ('016), ketones derived from 2-ethylbutyraldehyde and methyl alkyl ketones ('017), and C10 or greater ketones derived from 2-ethylbutyraldehyde and methyl alkyl ketones ('018). Temperature in the reaction zone is relatively low, with reaction times often longer than 10 hours. The reaction media is neutralized with dilute acid, filtered to remove salts, distilled, and hydrogenated to give saturated ketones. Several years prior to issuance of these patents, Powell, Journ. Amer. Chem. Soc., Vol. 46, 1924, pp. 2514–2517, laid out a similar process for the condensation of n-butyraldehyde with 2-butanone in the presence of alcoholic potassium hydroxide. Disadvantages for commercial application of these processes include the low temperature of operation, long reaction times, expensive alkoxide reagents, and the difficult recovery of product, complicated by the presence of the alcohol solvent.

U.S. Pat. No. 4,956,505 discloses a process for the condensation of pinacolone and p-chlorobenzaldehyde, in an alcohol as solvent, to give 4,4-dimethyl-1-(p-chlorophenyl) 3-penten-2-one, with subsequent hydrogenation to 4,4-dimethyl-1-(p-chlorophenyl)pentan-2-one. The condensation is catalyzed with 5–30, preferably 10–15 equivalents of alkali metal hydroxide base dissolved in C1 to C3 monohydric or polyhydric alcohols. The preferred solvent is methanol; particularly preferred is an amount of 20–40 weight percent of the reaction mixture. Although yields are reasonable, typically about 90% based on p-chlorobenzaldehyde, the reactions are slow and require expensive and complicated recycle of the solubilizing alcohol.

Several patents disclose the use of polymeric or oligomeric ethylene glycols or polyhydric alcohols, as phase transfer catalysts or solvents, in combination with dilute alkali metal hydroxide catalysts. U.S. Pat. No. 5,055,621 teaches the use of alkali metal hydroxide dissolved in a glycol, preferably diethylene glycol, optionally with water, for the condensation of benzaldehyde with straight-chain aldehydes to produce α-cinnamic aldehydes. U.S. Pat. No. 5,663,452 describes the aldol condensation of n-butyraldehyde in the presence of an alkali or alkali earth metal hydroxide dissolved in polyethylene glycol phase transfer catalyst. U.S. Pat. Publ. No.2002/0058846 teaches a process for the preparation of 6-methylheptan-2-one and corresponding homologous β-branched methylketones, in particular phytone and trathydrogeranyl acetone, by the two-liquid phase crossed condensation of acetone with 3-methyl-butanal, prenal or the like, in the presence of a dilute aqueous alkali or alkali earth metal hydroxide catalyst dissolved in a polyhydric alcohol for the aldol step, and a noble metal catalyst for hydrogenation. The polyhdric alcohol is preferably glycerol. All of these processes suffer from low reaction rates and complicated separation schemes for recovery and recycling of the phase transfer catalyst.

The category of amine-catalyzed condensation reactions includes U.S. Pat. Nos. 5,583,263 and 5,300,654. The category of heterogeneous catalysis with a metal or oxide on a solid support is exemplified by U.S. Pat. Nos. 5,936,131, 6,271,171, and 4,739,122.

A number of patents are directed solely to catalysts used to improve the selectivities and yields of aldol condensations. U.S. Pat. No. 4,146,581 to Nissen, et. al. describes a catalyst system for producing higher ketones; U.S. Pat. No. 4,270,006 to Heilen, et al. describes a catalyst system largely incorporating noble metals and salts of rare earth metals; U.S. Pat. No. 4,701,562 to Olson teaches a process for condensing aldehydes catalyzed by a nonzeolitic aluminophosphate; and U.S. Pat. No. 4,049,571 to Nissen, et. al. describes another catalyst for one-step aldol condensations that yield higher ketones.

Several authors have disclosed processes for crossed aldol condensations catalyzed by high levels of caustic. Weizmann and Garrard, J. Chem. Soc, Pt. 1, Vol. 117, 1920, pp. 324–338, prepared 3-hepten-2-one by the batch-wise crossed condensation of n-butyraldehyde and acetone catalyzed with solid sodium hydroxide. In their process, the aldehyde was fed in excess (ketone/aldehyde molar ratio of 0.96), with 0.055 equivalents of base per mole of aldehyde. No temperature control was attempted, the reaction times were 12 hours, and typical yields were about 30–35% based on n-butyraldehyde, with large quantities of the n-butyraldehyde self-condensation product, 2-ethyl-2-hexenal, observed.

Eccott and Linstead, J. Chem. Soc, Pt. 1, Vol.133, 1930, pp. 904–911, prepared a mixture of 4-hydroxy-2-heptanone and 3-hepten-2-one by the low-temperature, (5–10° C.) batch-wise crossed condensation of n-butyraldehyde and acetone catalyzed by 50 weight percent sodium hydroxide. In their process, the acetone was fed in excess (ketone/aldehyde molar ratio of 3.0), with 0.50 equivalents of base per mole of aldehyde. The high caustic to aldehyde loading and long reaction times resulted in typical yields of about 30% based on n-butyraldehyde. These authors failed to recognize the utility of catalyzing aldol condensation reactions with small amounts of concentrated alkali metal hydroxides providing relatively low amounts of water in the reaction mixture, with respect to the total weight of the reactants, nor did they recognize the proper reaction parameters, such as contacting mode, time, temperature, and concentrations, for optimizing conversion and selectivity.

There remains a need in the art for an aldol condensation process characterized by high yield and selectivity for β-hydroxy ketones and α,β-unsaturated ketones, that can be used over a wide range of temperatures, and that has relatively short reaction times.

BRIEF SUMMARY OF THE INVENTION

We have discovered that β-hydroxy-ketones and/or α,β-unsaturated ketones may be produced in unexpectedly high yields by the liquid-phase crossed condensation of an aldehyde with a ketone, in the presence of a small amount of a catalyst comprising a concentrated hydroxide or alkoxide of an alkali-metal (from Group 1 or Group IA of the Periodic Table of the Elements) or alkali-earth metal (from Group 2, or Group IIA of the Periodic Table of the Elements), wherein the amount of water present in the reaction mixture, or reaction zone, is relatively low, with respect to the total weight of the reactant mixture. Because water may be created by the dehydration of the β-hydroxy-ketone to the α,β-unsaturated ketone, the water concentration in the reaction mixture may optionally be adjusted to remain within the desired range, by removal of a portion of the water of reaction. An advantageous feature of the claimed invention is that reaction times can be thereby shortened, and in one aspect, the reaction mixture does not substantially separate into two distinct liquid phases throughout the reaction zone. The reaction can be carried out in the absence of solubilizing agents or phase transfer agents, and the product mixture is largely free of by-products resulting from further condensation reactions of the β-hydroxy-ketone, and the self-condensation reaction of the aldehyde.

All mention herein to elements of Groups of the Periodic Table, unless the context indicates otherwise, are made in reference to the Periodic Table of the Elements, as published in "Chemical and Engineering News", 63(5), 27, 1985. In this reference, the groups are numbered 1 to 18.

DETAILED DESCRIPTION OF THE INVENTION

A new process has been found for producing an aldol product (β-hydroxy-ketones and/or α,β-unsaturated ketones) with a combination of product selectivity and yield heretofore unrecognized in the art. According to the invention, one or more of: a β-hydroxy-ketone product of Formula III or an α,β-unsaturated ketone product of Formula IV are produced by the liquid-phase crossed condensation of an aldehyde reactant of Formula I with a ketone reactant of Formula II in the presence of a small amount of a catalyst comprising one or more bases, and especially a concentrated hydroxide or alkoxide of an alkali- or alkali-earth metal, wherein the amount of water present in the reaction mixture, or throughout the reaction zone, is relatively low, being no more than about 6 wt. %, with respect to the total weight of the reactant mixture.

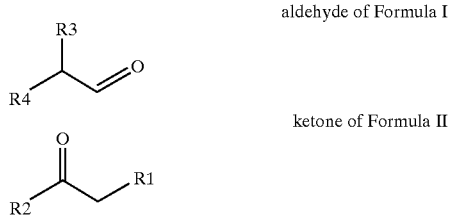

aldehyde of Formula I ketone of Formula II

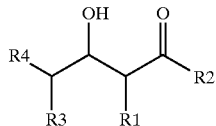

β-hydroxy-ketone of Formula III

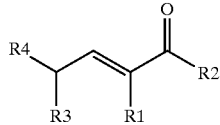

α-β unsaturated ketone of Formula IV

In one embodiment, R1 represents hydrogen, or else R1 and R2 form members of a common alicyclic ring of 4 to 12 carbon atoms, preferably 4 to 8 carbon atoms, and especially 5 to 6 carbon atoms, which alicyclic ring may be substituted with one or more branched or unbranched, saturated or unsaturated aliphatic or alkyl-substituted cycloaliphatic, or aromatic hydrocarbon radicals of 1 to 20 carbon atoms, preferably 1 to 12 carbon atoms, or with halogens or ether functionalities;

or else R2 represents a branched or unbranched, saturated or unsaturated aliphatic or alkyl-substituted cycloaliphatic hydrocarbon radical of 1 to 20 carbon atoms, preferably from 1 to 12 carbon atoms, or from 1 to 4 carbon atoms, and especially a methyl, ethyl, n-butyl, t-butyl, or i-butyl radical, which aliphatic or alkyl-substituted cycloaliphatic hydrocarbon radical may be substituted with halogens or ether functionalities; or else R2 represents a saturated or unsaturated alkyl-substituted cycloaliphatic hydrocarbon radical of 3 to 12 carbon atoms, preferably 3 to 8 carbon atoms, and especially 5 to 6 carbon atoms, which cycloaliphatic hydrocarbon radical may contain alkyl groups as substituents, and which may be substituted with halogens or ether functionalities; or else R2 represents an aryl hydrocarbon radical of 6 to 15 carbon atoms, preferably 6 to 9 carbon atoms, and especially a phenyl radical, which aryl hydrocarbon radical may be substituted with halogens or ether functionalities; or else R2 represents an alkylaryl hydrocarbon radical of 7 to 15 carbon atoms, preferably 7 to 10 carbon atoms, and especially a benzyl radical, which alkylaryl hydrocarbon radical may be substituted with halogens or ether functionalities;

R3, and R4 may each independently represent hydrogen, or else R3 and R4 form members of a common alicyclic ring of 4 to 12 carbon atoms, preferably from 4 to 8 carbon atoms, and especially 5 to 6 carbon atoms, such as a cyclohexyl radical, which alicyclic ring may be substituted with one or more branched or unbranched, saturated or unsaturated aliphatic or alkyl-substituted cycloaliphatic, or aromatic hydrocarbon radicals of 1 to 20 carbon atoms, preferably 1 to 12 carbon atoms, or with halogens or ether functionalities; or else R3 or R4 may represent a branched or unbranched, saturated or unsaturated aliphatic or alkyl-substituted cycloaliphatic hydrocarbon radical of 1 to 20 carbon atoms, preferably from 1 to 12 carbon atoms, and especially from 1 to 6 carbon atoms, such as a methyl, ethyl, n-propyl, or n-butyl radical, which aliphatic or cycloaliphatic hydrocarbon radical may be substituted with halogens or ether functionalities; or R3 or R4 may represent a saturated or unsaturated alkyl-substituted cycloaliphatic hydrocarbon radical of 3 to 12 carbon atoms, preferably from 3 to 8 carbon atoms, and especially from 5 to 6 carbon atoms, which cycloaliphatic hydrocarbon radical may contain alkyl groups as substituents, or which may be substituted with halogens or ether functionalities; or else R3 or R4 may represent an aryl hydrocarbon radical of 6 to 15 carbon atoms, preferably from 6 to 9 carbon atoms, and especially a phenyl radical, which aryl hydrocarbon radical may be substituted with halogens or ether functionalities; or else R3 or R4 may represent an alkylaryl hydrocarbon radical of 7 to 15 carbon atoms, preferably from 7 to 10 carbon atoms, and especially a benzyl radical, which alkylaryl hydrocarbon radical may be substituted with halogens or ether functionalities.

In a similar embodiment, R1, R3, and R4 each represent hydrogen, or R1, R2, R3, and R4 each represent a substituted or unsubstituted, straight or branched chain aliphatic radical containing 1 to 10 carbon atoms; a substituted or unsubstituted, straight or branched chain alkenyl radical containing 2 to 10 carbon atoms; a substituted or unsubstituted cycloalkyl or cycloalkenyl radical containing 4 to 10 carbon atoms; a substituted or unsubstituted aryl radical containing 6 to 10 carbon atoms, e.g., phenyl or napthyl; or a substituted or unsubstituted 4- to 10-membered heterocylic radical containing from 1 to 3 heteroatoms selected from oxygen and sulfur. The term "heterocyclic radical" denotes optionally substituted four to ten-membered rings that have 1 to 3 heteroatoms, selected independently from oxygen and sulfur. These four- to ten-membered rings may be saturated, partially unsaturated, or fully unsaturated.

The term "substituted" as used herein in conjunction with each of the above alkyl, alkenyl, cycloalkyl, cycloalkenyl, aryl, and heterocyclic radicals which may be represented by R1, R2, R3, and R4 denotes the above radicals substituted with one or more halogen, $C_1$–$C_6$-alkyl, $C_1$–$C_6$-alkoxy, substituted $C_1$–$C_6$-alkyl, $C_1$–$C_6$-alkylthio, aryl, arylthio, aryloxy, $C_2$–$C_6$-alkoxycarbonyl, $C_2$–$C_6$-alkanoylamino, hydroxy, carboxyl, cycloalkoxy, nitro, keto, thioether, aldehydo, carboalkoxy, imido, sulfinato, sulfanato, sulfonamide, sulfoxy, phosphato, cycloalkyl, amino, mono-substituted amino, di-substituted amino, acyloxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, acyloxy, acyl, alkyl, alkoxy, aminoacyl, acylamino, azido, carboxylalkyl, cyano, heteroaryl, heteroaryloxy, heterocyclyl, heterocyclooxy, aminoacyloxy, oxyacylamino, thioalkoxy, substituted thioalkoxy, thioaryloxy, thioheteroaryloxy, trihalomethyl, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, or arylcarbonylamino groups.

Examples of substituted and unsubstituted alkyl and alkenyl radicals include, but are not limited to, methyl, ethyl, cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl, n-propyl, isopropyl, isobutyl, n-butyl, tertiary butyl, pentyl, hexyl, 2-ethylhexyl, octyl, decyl, vinyl, 1-propenyl, 1-butenyl, 1-pentenyl, 2-octenyl, and various isomers thereof.

Examples of substituted and unsubstituted cycloalkyl and cycloalkenyl radicals include, but are not limited to, cyclopropyl, cyclobutyl, hydroxymethylcyclobutyl, cyclobutenyl, cyclopentyl, cyclopentenyl, cyclohexyl, cyclohexylcarbonyloxy, cyclohexenyl, cycloheptyl, 2-methylcyclopropyl, cycloheptenyl, 4-methylcyclohexyl, 3-methylcyclopentenyl, 4-(isopropyl)-cyclohexylethyl or 2-methyl-cyclopropylpentyl, and the like. Examples of heterocyclic radicals are tetrahydrofuranyl, tetrahydrothiofuranyl, thienyl, dioxanyl, pyranyl, furyl, chromenyl, xanthenyl, phenoxathiinyl, oxepane, oxathiolanyl, benzothienyl, and the like. Examples of substituted and unsubstituted aryl radicals are 4-chlorophenyl, 2,6-dichlorophenyl, 2,5-dichlorophenyl, 3,4-dichlorophenyl, 3-chlorophenyl, 3-bromophenyl, 4-bromoindenyl, 3,4-dibromophenyl, 3,4-dibromonaphthyl, 3-chloro-4-fluorophenyl, 2-fluorophenyl and the like; a mono- or di(hydroxy)aryl radical such as 4-hydroxyphenyl, 3-hydroxyphenyl, 2,4-dihydroxyphenyl, and the like; a nitroaryl group such as 3- or 4-nitrophenyl; a cyanoaryl group, for example, 4-cyanophenyl; a mono- or di(lower alkyl)aryl radical such as 4-methylphenyl, 2,4-dimethylphenyl, 2-methylnaphthyl, 4-(iso-propyl)-phenyl, 4-ethylnaphthyl, 3-(n-propyl)phenyl and the like; a mono- or di(alkoxy)aryl radical, for example, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl and the like; 3- or 4-trifluoromethylphenyl, a mono- or dicarboxyaryl radical such as 4-carboxyphenyl, 4-carboxynaphthyl; a mono- or di(hydroxymethyl)aryl radical such as 3,4-di(hydroxymethyl)phenyl, a mono- or di(aminomethyl)aryl radical such as 2-(aminomethyl) phenyl, or a mono- or di(methylsulfonylamino)aryl radical such as 3-(methylsulfonylamino)naphthyl. For the present process, it is preferred that R1 is methyl, phenyl, or vinyl; however, it is especially preferred that R1 is hydrogen.

In another, more general, embodiment, the invention relates to a process for producing an aldol product (one or more of a β-hydroxy-ketone product or an α,β-unsaturated ketone product), the process comprising reacting an aldehyde reactant with a ketone reactant, the ketone reactant having at least one hydrogen atom alpha to the carbonyl, in a reaction mixture comprising the aldehyde reactant, the ketone reactant, and a basic catalyst that can comprise a hydroxide or alkoxide of an alkali- or alkali-earth metal, wherein the basic catalyst (the hydroxide or alkoxide) is provided in a solution having a concentration of at least 15 wt. %, or as a solid, wherein no more than 6 wt. % water, based on the total of the water fed and water generated by reaction, is present in the reaction mixture, with respect to the total weight of the reaction mixture.

In yet a further embodiment, the invention relates to a process for preparing one or more of a compound of the formulas:

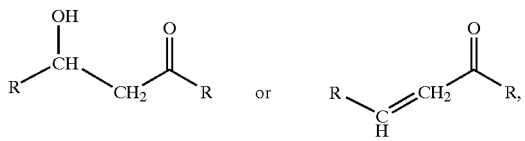

wherein each R is independently a hydrocarbyl group;

which comprises contacting in a reaction mixture a compound of the formula (i)

with a compound of the formula

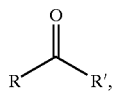

(ii)

wherein each R is independently a hydrocarbyl group, and R' is a hydrocarbyl group having at least one hydrogen atom on the carbon atom which serves as the point of attachment, in the presence of
  (iii) a catalyst comprised of a hydroxide or $C_1$–$C_8$ alkoxide of an alkali metal or alkaline earth metal, wherein the hydroxide or $C_1$–$C_8$ alkoxide of an alkali metal or alkaline earth metal is provided by at least one of:
    (a) in a solution having a concentration of at least 15 weight percent, or
    (b) as a solid,
  wherein no more than 6 weight percent water, based on the total weight of the water provided in the reaction mixture or the combination of water provided and water generated in situ is present in the reaction mixture upon completion, with respect to the total weight of the reaction mixture.

As used herein, a "hydrocarbyl" group means a monovalent or divalent, linear, branched, or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl or aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl or aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl or aryl. As used herein, the term "aryl" preferably denotes a phenyl, napthyl, or anthracenyl group. When the above groups are substituted, they are preferably substituted from one to four times with the listed groups. Examples of divalent (bridging hydrocarbyls) include: —$CH_2$—, —$CH_2CH_2$—, —$C_6H_4$—, and —$CH_2CH_2CH_2$—.

In another aspect, the amount of water provided to the reaction mixture, or reaction zone, is no more than about 2.5 wt. %, with respect to the total weight of the reactant mixture, though the water of reaction created during the reaction will increase the total amount of water present in the reaction mixture, over the course of the reaction. In this aspect, the initial amount of water provided in the reaction mixture is nonetheless no more than 2.5 wt. %, or no more than 2 wt. %, or even 1 wt. % or less.

When the desired product is the $\alpha,\beta$-unsaturated ketone, the yield of $\alpha,\beta$-unsaturated ketone may be increased by removal from the reaction zone of the water formed in the dehydration of the $\beta$-hydroxy-ketone to the $\alpha,\beta$-unsaturated ketone. The water of reaction may be removed from the reaction zone by any means known in the art, i.e., distillation, extraction, adsorption, or reaction. Generally, the yield of the $\alpha,\beta$-unsaturated ketone is maximized if less than 100% of the theoretical amount of water formed (assuming full conversion of the limiting reactant to the $\alpha,\beta$-unsaturated ketone) is removed from the reaction mixture, or when less than about 90% of the theoretical amount of water, or even less than about 80% of the theoretical amount of water generated is removed from the reaction mixture.

The process according to the claimed invention is further characterized by short reaction times. Reaction times are somewhat dependent on temperature and catalyst loading, but are typically less than 120 minutes, preferably less than 60 minutes, or less than 30 minutes, within the reaction zone. When operating in continuous plug flow mode, the residence time is preferably less than 30 minutes, more preferably less than 20 minutes, or even 10 minutes or less. We have unexpectedly found that longer reaction times result in a lowering of total yield, and an increase in unwanted side reactions. This is especially so when the base catalyst is provided in high concentration, and the total amount of water present in the reaction mixture is limited. Under these reaction conditions, it is important that the reaction time be limited.

Exemplary aldehydes for use in the process of the invention include, but are not limited to, acetaldehyde; propionaldehyde; n-butyraldehyde; 2-methyl-propanal; n-pentanal and structural isomers such as 2-methyl-butanal, 3-methylbutanal, and 2,2-dimethyl-propanal; n-hexanal and structural isomers such as 2-ethyl-butanal, 2,2-dimethylbutanal, 2,3-dimethylbutanal, 2-methyl-pentanal, 3-methylpentanal, and 4-methyl-pentanal; n-heptanal and structural isomers such as 2-methylhexanal, 2-ethylpentanal, 2,2-dimethylpentanal, 2,3-dimethylpentanal, 2,4-dimethylpentanal, 2-ethyl-3-methylbutanal, and 2-ethyl-2-methylbutanal; n-octanal and structural isomers such as 2-ethylhexanal, n-nonanal and structural isomers; n-decanal and structural isomers; n-undecanal and structural isomers; n-dodecanal and structural isomers; benzaldehyde; 4-chlorobenzaldehyde; 3-chlorobenzaldehyde; 2-chlorobenzaldehyde; phenyl acetaldehyde; o-tolualdehyde; m-tolualdehyde; p-tolualdehyde; p-methoxybenzaldehyde; o-methoxybenzaldehyde; m-methoxybenzaldehyde; cyclopropane carboxaldehyde; cyclobutane carboxaldehyde; cyclopentane carboxaldehyde; cyclohexane carboxaldehyde; 2-methylcyclohexane carboxaldehyde; 3-methylhexane carboxaldehyde; 4-methylhexane carboxaldehyde.

Exemplary ketones for use in the process of the invention include, but are not limited to, acetone, 2-butanone, 2-pentanone, 3-methyl-2-butanone, 2-hexanone, 4-methyl-2-pentanone, 3-methyl-2-pentanone, pinacolone, 2-heptanone, 5-methyl-2-hexanone, 2-octanone, 2-nonanone, 2-decanone, 2-undecanone, 2-dodecanone, cyclobutanone, cyclopentanone, cyclohexanone, acetophenone. Preferred ketones are methyl ketones.

The reactants can be either liquids or solids at room temperature. It is preferred that there be low levels, generally less than 1–2%, of the corresponding acid derived from the aldehyde reactant. This acid, if present, tends to neutralize the small amount of base used as catalyst. Thus, one must add sufficient caustic to neutralize the acid, then provide a caustic/aldehyde ratio within the specifications of the invention (above that of the acid present). Feeds with higher levels of acid may be used, but result in expensive and unnecessarily high catalyst usage. For example, if n-butyraldehyde contaminated with 5 wt % n-butyric acid were condensed with acetone using 0.01 equivalents of 50% caustic catalyst per mole of n-butyraldehyde, according to the invention, then an additional 0.04 equivalents of caustic per mole of butyraldehyde would be added to the feed to neutralize the butyric acid. Thus, the catalyst usage is 5 times higher when the acid contaminant is present in the feed at the 5 wt % level.

Products according to the claimed process include, but are not limited to, 4-hydroxy-2-heptanone, 3-hepten-2-one, 3-hydroxy-2-ethylhexanal, 2-ethyl-2-hexenal, 7-ethyl-2-methylundec-5-en-4-one, 4-hydroxy-6-undecanone, 3-undecen-6-one, 4-hydroxy-5-methyl-2-hexanone, 5-methyl-3-hexen-2-one, 4-hydroxy-6-nonanone, 4-nonen-6-one, 4,4-dimethyl-1-(p-chlorophenyl)-1-penten-3-one, 1-(p-chlorophenyl)-1-buten-3-one, 1-cyclohexyl-1-buten-3-one, and 1-hydroxy-1-cylclohexyl-3-butanone.

The reaction temperature can be chosen, in general, within a wide range, i.e., between about 0° C. to 200° C. Preferably, it is between 25° C. and 175° C., more preferably between 40° C. and 165° C., or between 50° and 160° C.

The pressure is chosen such that the reaction mixture remains as a liquid throughout the reaction zone, generally from about 1 to about 70 atmospheres, depending on temperature and reactants, or from 1 to 45 atmospheres.

According to the invention, the molar ratio of ketone and aldehyde concentration in the reaction zone can be varied over a wide range. To avoid the separation and recycle of unnecessarily large amounts of ketone, in general 1 to 20 moles of ketone are used per mole of aldehyde, more preferably from 1 to 14 moles of ketone per mole of aldehyde, or from 1.05 to 10 moles per mole.

Suitable catalysts for the condensation reaction are the hydroxides or alkoxides of alkali metals (Group I) or alkaline earth metals (Group II). These include, but are not limited to, sodium hydroxide, potassium hydroxide, cesium hydroxide, lithium hydroxide, magnesium hydroxide, calcium hydroxide, barium hydroxide, sodium methoxide, sodium ethoxide, sodium propoxide, sodium butoxide, potassium methoxide, potassium ethoxide, potassium propoxide, potassium butoxide, cesium methoxide, cesium ethoxide, cesium propoxide, cesium butoxide, lithium methoxide, lithium ethoxide, lithium propoxide, lithium butoxide, magnesium methoxide, magnesium ethoxide, magnesium propoxide, magnesium butoxide, calcium methoxide, calcium ethoxide, calcium propoxide, calcium butoxide, barium methoxide, barium ethoxide, barium propoxide, barium butoxide. Further suitable bases are the oxides of the elements mentioned, which under the reaction conditions can form the hydroxides. Preferably, sodium hydroxide or potassium hydroxide are used because they are readily available and inexpensive. It is also possible to use mixtures of different stoichiometric amounts of the aforementioned compounds as the aldolization catalyst The amount of the catalyst (base) to be added can vary within wide limits. However, it has been found that between 0.001 to 0.45 equivalents, preferably between 0.005 to 0.15 equivalents of base, and especially 0.005 to 0.10 equivalents relative to the molar amount of aldehyde, are sufficient and thus help to avoid an unnecessarily high consumption of base, as well as to avoid formation of a separate and distinct catalyst-containing phase. When operating in continuous plug flow mode, the molar ratio of catalyst to aldehyde is more preferably between 0.005 and 0.10. The base can be added to the reaction mixture either as such or in dissolved form. They are preferably used in dissolved form.

The concentration of catalyst, or base, useful according to the invention can likewise vary, although higher concentrations than are typically used in the art are a feature of the claimed invention. According to the invention, the catalyst is provided as an aqueous solution, with a concentration of at least 15 wt. %, or at least 20 wt. %, or at least 25 wt. %, and even at 50 wt. % or more, although the catalyst can be provided as a 100 wt. % solid. Particularly satisfactory results are obtained with a catalyst concentration of 25 wt. % or above. We have found that the concentration of the aqueous solution used, perhaps by adding to the total amount of water present in the reaction mixture, can affect the yield and selectivity for the target product, and that relatively small amounts of a higher concentration catalyst are much preferred.

In this regard, it is important according to the invention that the total amount of water present throughout the reaction zone, with respect to the total weight of reactants, be limited. In this aspect of the invention, the total amount of water present includes the water present in the reaction mixture initially, as well as the water of reaction created during the course of the reaction, minus any water removed during the reaction, for example via distillation. Thus, in one aspect, the amount of water present in the reaction mixture, or throughout the reaction zone, is no more than about 6 wt %, based on the total weight of the reaction mixture. In another aspect, the amount of water present is no more than 4 wt. %, or no more than 3 wt. %, or even 2 wt. % or less. Not being bound by any theory, we believe that limiting the amount of water present in the reaction mixture, with respect to the total weight of reactants, may alter the solvating environment around the alkali or alkaline earth metal catalyst which favors an enhancement of the cross-aldol, versus self-aldol, condensation ratio. This enhancement may be due to the preferred coordination of the alkali or alkaline earth metal catalyst to the carbonyl of a reactive ketone or aldehyde.

When the desired product of the invention is primarily the $\alpha,\beta$-unsaturated ketone, and depending on the aldehyde and ketone substrates being used, the overall equilibrium of the aldol condensation reaction coupled with the dehydration reaction may be unfavorable for significant formation of the $\alpha,\beta$-unsaturated ketone. To some extent, unfavorable equilibria may be compensated for by the conditions chosen for the reaction zone, i.e., by proper selection of temperature, pressure, and ketone-to-aldehyde feed ratio, within the scope of the invention.

Alternatively, one may drive the formation of the $\alpha,\beta$-unsaturated ketone by removal of one of the products of the dehydration reaction from the reaction zone. Typically, water is the most convenient product to remove. Thus, by LeChatelier's principle, removal of water from the reaction zone shifts the equilibrium of the coupled condensation-dehydration reactions toward formation of the $\alpha,\beta$-unsaturated ketone from the $\beta$-hydroxy-ketone, as well as leading to higher consumption of the limiting reactant, typically the aldehyde.

Water may be removed from the reaction zone by carrying out a separation simultaneously with the reaction. Many means for accomplishing the separation of water from the reaction zone are well-known in the art. These include distillation, extraction, continuous chromatography such as simulated moving bed chromatography, pervaporation, or adsorption onto hydrophilic media such as molecular sieves, or silica gel. The inherent acidity of many hydrophilic molecular sieves limits their usefulness; they tend to neutralize the base that is present for catalysis of the condensation reaction.

Alternatively, water may, in effect, be removed from the reaction zone by chemical complexation or reaction. Examples of suitable complexation compounds include, but are not limited to, anhydrous magnesium sulfate, calcium sulfate, and sodium sulfate. Examples of suitable reactants include, but are not limited to, barium oxide and calcium hydride. These two reactants form hydroxides upon reaction with water, and thus also may function as catalysts according to the present invention.

The preferred method for removal of water is by generation and removal of water-laden vapors, i.e., distillation, from the reaction zone. Distillative removal of water is most favored when the reactant ketone or aldehyde, or both, form heterogeneous azeotropes with water and both the aldehyde and ketone have normal boiling points greater than about 70° C. In one embodiment of distillative removal of water from the reaction zone, in which a reactant forms a heterogeneous azeotrope with water, the reactant mixture is heated to its boiling point while being allowed to react. The vapors thus generated are condensed, collected, and allowed to separate into two liquid layers. The organic-rich layer is returned to the reaction zone and the water-rich layer is removed for further processing. Other embodiments of distillative removal of water are possible. Such a water removal scheme may be carried out in equipment well-known in the art such as a stirred tank reactor fitted with a vapor take-off line or a column section.

We have found that the extent of water removal performed during the reaction step significantly affects the ultimate yield of the process. Excessive removal of water tends to lead to formation of higher boiling or oligomeric by-products resulting from further reaction of the $\alpha,\beta$-unsaturated ketone. The theoretical water of reaction is defined here as the water that would be generated by complete conversion of the limiting reactant, usually the aldehyde, to the $\beta$-hydroxy ketone, and subsequent complete dehydration to the $\alpha,\beta$-unsaturated ketone. Thus we have found that it is desirable to remove less than about 100%, or less than about 90%, and preferably less than about 80%, of the theoretical amount of the water of reaction, to maximize yields of the $\alpha,\beta$-unsaturated ketone.

The process according to the invention can be carried out batchwise or continuously. When carried out batchwise, the reaction zone may comprise any reactor format in which the exothermic heat of reaction can be removed or controlled. Examples of preferred batch reaction formats are stirred tanks with temperature-controlled jackets, internal heat exchanger coils, or an external heat-exchanged pump around loop. The temperature may also be controlled by evaporative cooling of the reaction mixture. Typically, the vapors thus generated are condensed and refluxed to the batch reaction zone. Preferably, the reaction zone is operated isothermally, although it may be possible to operate the reaction zone according to a temperature program—i.e., ramping up or down, or varying the temperature over the course of the reaction.

When the process according to the invention is carried out continuously, the reaction zone preferably comprises or approximates an ideal plug flow reactor, such as a tubular or multi-tubular reactor, or a cascade of stirred tanks. The reaction zone may be operated adiabatically (no external heat added or internally generated heat removed), or isothermally (at a constant temperature), or a combination thereof. When the reaction zone comprises a tubular reactor, the exothermic heat of reaction may be controlled by any means known in the art, and may comprise, for example, a staged tubular reactor with interstage heat exchange, cold-shotting of ketone reactant into a multi-stage tubular reactor, an annular temperature-controlled jacketed tubular reactor, or a shell-and-tube heat exchanger. When the reaction zone comprises a cascade of stirred tanks, heat removal may be accomplished by the use of stirred tanks with temperature-controlled jackets, internal heat exchanger coils, or an external heat-exchanged pump around loop. The temperature may also be controlled by evaporative cooling of the reaction mixture. The aldehyde and ketone may be fed separately or as a mixture. Generally it is preferable to feed the aldehyde and ketone as a mixture. In particular, if either the aldehyde or ketone is a solid and cannot be melted readily, then it is preferable to dissolve the solid feed component in the liquid feed component. Generally it is sufficient to provide one feed port in the reaction zone, but multiple feed points may be used. The aldehyde to ketone feed ratio may vary between the multiple feed points, but this is not necessary.

When the reaction zone comprises a cascade of stirred tanks, it is preferable to add the catalyst-as a separate feed stream from the aldehyde. If the catalyst is mixed with the reactants, outside of the reaction zone, then uncontrolled reaction may occur prematurely.

When the amount of catalyst used is low compared to the amount of the reactants (i.e., less than about 0.5% of the total feed mixture), then it may be desirable to mix the catalyst with a portion of the ketone reactant prior to addition to the reaction zone. This assists in accurately metering the small amount of catalyst used.

When the reaction zone comprises a tubular reactor, the catalyst should be combined with the reactants in a well-mixed environment, that is in a section of the reactor where the flow is turbulent, i.e., having a Reynolds number greater than at least about 2,000, or in a section containing mixing elements.

The tubular reactor that may be used in the process of the invention may contain inert packing elements or internal fitments, or static mixers, to improve mixing and heat transfer. Packing elements for the purposes of the present invention include, for example, Raschig rings, saddles, Pall rings, Tellerettes, wire mesh rings, wire mesh fabrics, or other forms of static mixers well-known in the art.

In one aspect, the reaction mixture generally does not separate into two distinct liquid phases throughout the reaction zone. By this we mean that the two phases remain substantially mixed throughout the reaction zone, either as miscible liquids or as a fine emulsion in which the immiscible dispersed phase is held in a stable suspension in the continuous phase under reaction conditions while in the reaction zone.

In a significant aspect, the process according to the invention is carried out in the substantial absence of any compatibilizing agents, solubilizing agents, or phase transfer agents. "Substantial absence" means that these agents are not added to the reaction mixture as such, nor are they intentionally generated in situ. While one or more of these agents may inadvertently be generated during reaction, they are nonetheless not present in the reaction mixture in appreciable amounts.

Categories of these compatibilizing agents or phase transfer agents include, but are not limited to, alkanols, polyols, and polyether alcohols, and other compounds known in the art to be surfactants, such as carboxylic acid salts, sulfonates, ethoxylates, amines, and amides. These agents are generally characterized by their ability to reduce the interfacial tension of normally immiscible liquids. Examples of such agents include, but are not limited to, carboxylic acid salts of the corresponding reactant aldehyde; alkanols containing one to 6 carbon atoms, such as methanol, ethanol, propanol, isopropanol, butanol, isobutanol, pentanol and its C-5 analogs, and hexanol and its C-6 analogs; glycerol or another sugar alcohol; ethylene glycol; diethylene glycol; propylene glycol; dipropylene glycol; 1,3-propanediol; 1,2-propanediol; butylene glycols;erythritol and isomeric tetrahydric alcohols; pentaerythritol; various pentahydric alcohols such as arabitol and xylitol; hexahydric alcohols; polyhydric alcohols not derived from sugar alcohols, such as inositol, and related compounds, isomers, and homologs; salts of aromatic sulfonic acids; polyethylene glycol; polypropylene glycol; diglyme, triglyme, and tetraglyme. By not adding these compatibilizing or phase transfer agents to the reaction mixture, subsequent separation steps are thereby avoided.

Solubilizing agents may nonetheless be introduced into the reaction zone, for example if an alkanol solution of an alkali metal or alkaline earth metal alkoxide is used as the catalyst. For example, sodium methoxide is available in commercial quantities as a 50 wt % solution in methanol. If the catalyst-to-aldehyde ratio is kept within the scope of the invention while using such an alkoxide catalyst, then the alcohol in which the alkoxide is provided is not present in sufficient quantities to act as a solubilizing agent according to the practice in the prior art (see, for example, U.S. Pat. Nos. 2,088,015 ('015), 2,0880,016 ('016), 2,0880,017 ('017), and 2,088,018 ('018). If these solubilizing agents are introduced into the reaction zone as part of the catalyst feed, the amount is preferably no more than 8 wt. %, based on the total weight of reactants, more preferably no more than 5 wt. %, or no more than 2 wt. %, or 1 wt. %, or less.

The examples which follow are intended to illustrate the process according to the invention, but without limiting it thereto.

EXAMPLES

The invention can be further illustrated by the following examples of preferred embodiments, although it will be understood that these examples are included merely for purposes of illustration and are not intended to limit the scope of the invention unless otherwise specifically indicated.

For all examples and counterexamples described herein, conversion and selectivity terms are defined as follows:

$$\% \text{ Conversion of aldehyde} = \frac{\text{moles aldehyde reacted}}{\text{moles aldehyde in feed}}$$

$$\% \text{ Selectivity to } \beta\text{-hydroxy ketone} = \frac{\text{moles } \beta\text{-hydroxy ketone formed}}{\text{moles aldehyde reacted}}$$

$$\% \text{ Selectivity to 3-hepten-2-one} = \frac{\text{moles 3-hepten-2-one formed}}{\text{moles n-butyraldehyde reacted}}$$

$$\% \text{ Selectivity to aldehyde self-condensation products} =$$

$$\frac{2 * \text{moles } \beta\text{-hydroxy aldehyde} + \alpha,\beta\text{-unsaturated aldehyde formed}}{\text{moles aldehyde reacted}}$$

Unless otherwise stated, all analyses were done by gas chromatography using a Hewlett-Packard model 5890 gas chromatograph, equipped with a DB-5 column, TC detector, and auto injector. For each analysis, the initial temperature of the column was set at 35° C., held for 2 minutes, and ramped to 250° C. at a rate of 20° C. per minute, and held for 2 to 5 minutes at 250° C.

Example 1

32.54 grams of acetone and 2.99 grams of n-butyraldehyde were charged to a 100 ml autoclave fitted with a magnetic stirrer, nitrogen purge, cooling coil, temperature-controlled band heater, and blow case for introduction of reactants and catalysts under pressure. The blow case was charged with 3.63 grams of acetone and 0.0717 grams of 50% aqueous sodium hydroxide solution and valved-off from the reactor vessel. These specifications gave a total feed of 13 moles of acetone per mole of n-butyraldehyde and 0.08 moles caustic per mole of n-butyraldehyde. The total amount of water present in the reaction mixture at the start of the reaction, based on the total weight of reactants, was thus about 0.38%. The autoclave was sealed, purged with nitrogen, and heated to 60° C., while stirring at 1800 rpm. Once a stable temperature had been reached the blow case was pressurized with nitrogen and the valve was opened to allow introduction of the blow case contents into the reaction vessel. The contents of the reactor were maintained at 60° C. and sampled periodically to determine percent conversion of n-butyraldehyde, selectivity to 4-hydroxy-2-heptanone (4H2H), 3-hepten-2-one (3E2H), and a combined total of 3-hydroxy-2-ethylhexanal and 2-ethyl-2-hexenal (EHA). Samples were cooled to about 17° C. as collected and quenched by buffering to pH=7. All analyses were done by gas chromatography. A summary of reaction conditions and results for 50% and 96% conversion is given in Table 1. The calculated combined total amount of water in the reaction mixture at the end of the reaction, including both the amount of water provided at the start of the reaction, as well as the water of reaction created during the course of the reaction, was calculated to be 1.1 wt. %, based on the total weight of reactants.

Example 2

36.65 grams of acetone and 1.39 grams of 50% aqueous sodium hydroxide solution were charged to a 100 ml autoclave fitted with a magnetic stirrer, nitrogen purge, cooling coil, temperature-controlled band heater, and blow case for introduction of reactants and catalysts under pressure. The blow case was charged with 3.40 grams of n-butyraldehyde and valved-off from the reactor vessel. These specifications gave a total feed of 13.4 moles of acetone per mole of n-butyraldehyde and 0.37 moles caustic per mole of n-butyraldehyde. The total amount of water present in the reaction mixture at the start of the reaction, based on the total weight of reactants, was thus about 1.7 wt. %. The autoclave was sealed, purged with nitrogen, and heated to 90° C., while stirring at 1800 rpm. Once a stable temperature had been reached the blow case was pressurized with nitrogen and the valve was opened to allow introduction of the blow case contents into the reaction vessel. The contents of the reactor were maintained at 90° C. and sampled periodically to determine percent conversion of n-butyraldehyde, selectivity to 4-hydroxy-2-heptanone (4H2H), 3-hepten-2-one (3E2H), and a combined total of 3-hydroxy-2-ethylhexanal and 2-ethyl-2-hexenal (EHA). Samples were cooled to about 10° C. as collected and quenched by buffering to pH=7. All analyses were done by gas chromatography. A summary of reaction conditions and results for 50% and 96% conversion is given in Table 1. The calculated combined total amount of water in the reaction mixture at the end of the reaction, including both the amount of water provided at the start of the reaction, as well as the water of reaction created during the course of the reaction, was calculated to be 2.9 wt. %, based on the total weight of reactants.

Example 3 (Comparative)

36.42 grams of acetone, 17.0 grams of water, and 3.49 grams of n-butyraldehyde were charged to a 100 ml autoclave fitted with a magnetic stirrer, nitrogen purge, cooling coil, temperature-controlled band heater, and blow case for introduction of reactants and catalysts under pressure. The blow case was charged with 1.8 grams of water and 1.26 grams of 50% aqueous sodium hydroxide solution and valved-off from the reactor vessel. These specifications gave a total feed of 13 moles of acetone per mole of n-butyraldehyde and 0.325 moles caustic per mole of n-butyraldehyde. The total amount of water present in the reaction mixture at the start of the reaction, based on the total weight of reactants, was thus about 32.3 wt. %. The autoclave was sealed, purged with nitrogen, and heated to 80° C., while stirring at 1800 rpm. Once a stable temperature had been reached the blow case was pressurized with nitrogen and the valve was opened to allow introduction of the blow case contents into the reaction vessel. The contents of the reactor were maintained at 80° C. and sampled periodically to determine percent conversion of n-butyraldehyde, selectivity to 4-hydroxy-2-heptanone (4H2H), 3-hepten-2-one (3E2H), and a combined total of 3-hydroxy-2-ethylhexanal and 2-ethyl-2-hexenal (EHA). Samples were cooled to about 17° C. as collected and quenched by buffering to pH=7. All analyses were done by gas chromatography. A summary of reaction conditions and results for 50% and 96% conversion is given in Table 1. The calculated combined total amount of water in the reaction mixture at the end of the reaction, including both the amount of water provided at the start of the reaction, as well as the water of reaction created during the course of the reaction, was calculated to be 33.3 wt. %, based on the total weight of reactants.

Example 4 (Comparative)

35.78 grams of acetone and 0.95 grams of water-wet Amberlyst® A-26 strongly basic quaternary ammonium hydroxide resin in the hydroxyl form were charged to a 100 ml autoclave fitted with a magnetic stirrer, nitrogen purge, cooling coil, temperature-controlled band heater, and blow case for introduction of reactants and catalysts under pressure. The blow case was charged with 2.995 grams of n-butyraldehyde and valved-off from the reactor vessel. These specifications gave a total feed of 14.8 moles of acetone per mole of n-butyraldehyde and a 2 weight percent resin loading in the reactor. The autoclave was sealed, purged with nitrogen, and heated to 60° C., while stirring at 1800 rpm. Once a stable temperature had been reached the blow case was pressurized with nitrogen and the valve was opened to allow introduction of the blow case contents into the reaction vessel. The contents of the reactor were maintained at 60° C. and sampled periodically to determine percent conversion of n-butyraldehyde, selectivity to 4-hydroxy-2-heptanone (4H2H), 3-hepten-2-one (3E2H), and a combined total of 3-hydroxy-2-ethylhexanal and 2-ethyl-2-hexenal (EHA). Samples were cooled to about 17° C. as collected and quenched by buffering to pH=7. All analyses were done by gas chromatography. A summary of reaction conditions and results for 50% and 96% conversion is given in Table 1.

Examples 5–7 (Inventive), and Examples 8–9 (Comparative)

A standard solution was prepared, consisting of 49.27 grams of acetone mixed with 15.51 grams of n-butyraldehyde. The molar ratio of acetone to butyraldehyde in the standard solution was 3.9. For Examples 5–7 and Counterexamples 7 and 8, the solution was then divided into approximately equal sized portions and poured into five 4-dram capped vials. A teflon-coated stir bar was used for agitation, and each vial was placed on a magnetic stirring plate. Solid sodium hydroxide pellets and solutions of 50%, 28%, 12.5%, and 5% aqueous sodium hydroxide were prepared and added at time zero to each of the five vials. The vials were sealed, stirred, and allowed to react initially at room temperature. The vials were sampled 22 minutes after introduction of the caustic catalyst. The samples were cooled to about 17° C. as collected and quenched by buffering to pH=7. All analyses were done by gas chromatography.

Example 5

8.71 grams of the standard solution were mixed with 0.22 grams of solid NaOH pellets and sealed. The molar ratio of acetone to n-butyraldehyde was 3.9. The molar ratio of sodium hydroxide to n-butyraldehyde was 0.19. Water content at the beginning of the experiment was 0.0 weight percent. The solution did not separate into multiple liquid phases throughout the course of the experiment, although a small amount of white solid, presumed to be sodium hydroxide, did form. After 22 minutes reaction time, the conversion of n-butyraldehyde was greater than 90% and the molar selectivity to 4-hydroxy-2-heptanone and 3-hepten-2-one was 85%. The calculated total amount of water present in the reaction mixture at the end of the reaction, which in this case was only the water of reaction created during the course of the reaction, was calculated to be less than 4.8 wt. %, based on the total weight of reactants.

Example 6

8.63 grams of the standard solution were mixed with 0.3 grams of 50 weight percent aqueous NaOH and sealed. The molar ratio of acetone to n-butyraldehyde was 3.9. The molar ratio of sodium hydroxide to n-butyraldehyde was 0.13. Water content at the beginning of the experiment was about 1.7 weight percent. The solution did not separate into multiple liquid phases throughout the course of the experiment. After 22 minutes reaction time, the conversion of n-butyraldehyde was greater than 90% and the molar selectivity to 4-hydroxy-2-heptanone and 3-hepten-2-one was 90%. The calculated combined total amount of water in the reaction mixture at the end of the reaction, including both the amount of water provided at the start of the reaction, as well as the water of reaction created during the course of the reaction, was calculated to be less than 6 wt. %, based on the total weight of reactants.

Example 7

8.60 grams of the standard solution were mixed with 0.38 grams of 50 weight percent aqueous NaOH, 0.3 grams water, and sealed. The molar ratio of acetone to n-butyraldehyde was 3.9. The molar ratio of sodium hydroxide to n-butyraldehyde was 0.17. Water content at the beginning of the experiment was 2.1 weight percent. The solution did not separate into multiple liquid phases throughout the course of the experiment. After 22 minutes reaction time, the conversion of n-butyraldehyde was greater than 90% and the molar selectivity to 4-hydroxy-2-heptanone and 3-hepten-2-one was 79%. The calculated combined total amount of water in the reaction mixture at the end of the reaction, including both the amount of water provided at the start of the reaction, as well as the water of reaction created during the course of the reaction, was calculated to be less than 6 wt. %, based on the total weight of reactants.

Example 8 (Comparative)

8.61 grams of the standard solution were mixed with 0.35 grams of 50 weight percent aqueous NaOH, 1.05 grams water, and sealed. The molar ratio of acetone to n-butyraldehyde was 3.9. The molar ratio of sodium hydroxide to n-butyraldehyde was 0.15. Water content at the beginning of the experiment was 12.2 weight percent. The solution was observed to separate into multiple liquid phases by the end of the experiment. After 22 minutes reaction time, the conversion of n-butyraldehyde was greater than 90% and the molar selectivity to 4-hydroxy-2-heptanone and 3-hepten-2-one was 58%. The calculated combined total amount of water in the reaction mixture at the end of the reaction, including both the amount of water provided at the start of the reaction, as well as the water of reaction created during the course of the reaction, was calculated to be 16.8 wt. %, based on the total weight of reactants.

Example 9 (Comparative)

8.70 grams of the standard solution were mixed with 0.35 grams of 50 weight percent aqueous NaOH, 3.17 grams water, and sealed. The molar ratio of acetone to n-butyraldehyde was 3.9. The molar ratio of sodium hydroxide to n-butyraldehyde was 0.15. Water content at the beginning of the experiment was about 27 weight percent. The solution was observed to separate into multiple liquid phases throughout the experiment. After 22 minutes reaction time, the conversion of n-butyraldehyde was greater than 90% and the molar selectivity to 4-hydroxy-2-heptanone and 3-hepten-2-one was 55%. The calculated combined total amount of water in the reaction mixture at the end of the reaction, including both the amount of water provided at the start of the reaction, as well as the water of reaction created during the course of the reaction, was calculated to be 31.2 wt. %, based on the total weight of reactants.

Examples 10–22

For examples 10–22, the reaction zone comprised a series of three 100 foot long stainless steel tubes of 0.086-inch inside diameter which were coiled within separate jacketing pipes. Heat transfer fluid circulated through the pipe jackets to maintain essentially isothermal conditions throughout the reaction zone. The reaction zone was fitted with sampling ports after each of the three sections of tubing. Pressure was sufficient to keep the reaction mixture as a liquid through the reaction zone. Pressure was maintained by a back pressure regulator at the outlet of the reaction zone. Mixtures of acetone and n-butyraldehyde were premixed in a ten gallon stainless steel tank and pumped at the desired flow rate into the reaction zone via a feed preheater consisting of a jacketed 100-foot coiled tube identical to those of the reaction zone. The aqueous sodium hydroxide catalyst solution of the desired concentration was loaded into a syringe pump at the start of the experiment. The catalyst solution was introduced into the reactant feed mixture via a tee in the tubing just prior to the reaction zone and after the feed preheater. The reactants and catalyst were allowed to flow through the reaction zone for at least 15 minutes prior to sampling to ensure steady state operation. Samples were collected to determine percent conversion of n-butyraldehyde, molar selectivity to 4-hydroxy-2-heptanone and 3-hepten-2-one, the ratio of 3-hepten-2-one to 4-hydroxy-2-heptanone, and molar selectivity to 3-hydroxy-2-ethylhexanal and 2-ethyl-2-hexenal. Samples were quenched by buffering to pH=7. All analyses were done by gas chromatography.

Example 10

The reaction was conducted in the plug flow apparatus described above. A mixture of acetone to n-butyraldehyde (7.4 molar ratio) was fed at 150 ml/min, preheated to 101.5° C., and mixed with 0.15 ml/min of 50% caustic (0.012 molar ratio of caustic to n-butyraldehyde) prior to entering the reaction zone. The total amount of water present in the reaction mixture at the start of the reaction, based on the total weight of reactants, was thus about 0.095 wt. %. The reaction zone was sampled after the third reactor section to give a residence time of about 2 minutes, with an outlet temperature of 108.4° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.3 wt. %, based on the total weight of reactants.

Example 11

The reaction was conducted in the plug flow apparatus described above. A mixture of acetone to n-butyraldehyde (7.4 molar ratio) was fed at 150 ml/min, preheated to 78.4° C., and mixed with 0.15 ml/min of 50% caustic (0.012 molar ratio of caustic to n-butyraldehyde) prior to entering the reaction zone. The total amount of water present in the reaction mixture at the start of the reaction, based on the total weight of reactants, was thus about 0.095 wt. % The reaction zone was sampled after the third reactor section to give a residence time of about 2.1 minutes, with an outlet temperature of 82° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.16 wt. %, based on the total weight of reactants.

Example 12

The reaction was conducted in the plug flow apparatus described above. A mixture of acetone to n-butyraldehyde (7.4 molar ratio) was fed at 150 ml/min, preheated to 91.8° C., and mixed with 0.45 ml/min of 50% caustic (0.036 molar ratio of caustic to n-butyraldehyde) prior to entering the reaction zone. The total amount of water present in the reaction mixture at the start of the reaction, based on the total weight of reactants, was thus about 0.28 wt. %. The reaction zone was sampled after the first reactor section to give a residence time of about 0.7 minutes, with an outlet temperature of 95.7° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.59 wt. %, based on the total weight of reactants.

Example 13

The reaction was conducted in the plug flow apparatus described above. A mixture of acetone to n-butyraldehyde (7.4 molar ratio) was fed at 150 ml/min, preheated to 91.8° C., and mixed with 0.075 ml/min of 50% caustic (0.006 molar ratio of caustic to n-butyraldehyde) prior to entering the reaction zone. The total amount of water present in the reaction mixture at the start of the reaction, based on the total weight of reactants, was thus about 0.047%. The reaction zone was sampled after the third reactor section to give a residence time of about 0.7 minutes, with an outlet temperature of 95.8° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.047 wt. %, based on the total weight of reactants.

Example 14

The reaction was conducted in the plug flow apparatus described above. A mixture of acetone to n-butyraldehyde (7.4 molar ratio) was fed at 150 ml/min, preheated to 106.8° C., and mixed with 0.30 ml/min of 50% caustic (0.024 molar ratio of caustic to n-butyraldehyde) prior to entering the reaction zone. The total amount of water present in the reaction mixture at the start of the reaction, based on the total weight of reactants, was thus about 0.19 wt. %. The reaction zone was sampled after the third reactor section to give a residence time of about 2 minutes, with an outlet temperature of 113.6° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.26 wt. %, based on the total weight of reactants.

Example 15

The reaction was conducted in the plug flow apparatus described above. A mixture of acetone to n-butyraldehyde (12.4 molar ratio) was fed at 150 ml/min, preheated to 59.6° C., and mixed with 0.15 ml/min of 50% caustic (0.019 molar ratio of caustic to n-butyraldehyde) prior to entering the reaction zone. The total amount of water present in the reaction mixture at the start of the reaction, based on the total weight of reactants, was thus about 0.095 wt. %. The reaction zone was sampled after the first reactor section to give a residence time of about 0.7 minutes, with an outlet temperature of 61.2° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.14 wt. %, based on the total weight of reactants.

Example 16

The reaction was conducted in the plug flow apparatus described above. A mixture of acetone to n-butyraldehyde (12.4 molar ratio) was fed at 150 ml/min, preheated to 92.2° C., and mixed with 0.15 ml/min of 50% caustic (0.019 molar ratio of caustic to n-butyraldehyde) prior to entering the reaction zone. The total amount of water present in the reaction mixture at the start of the reaction, based on the total weight of reactants, was thus about 0.095 wt. %. The reaction zone was sampled after the first reactor section to give a residence time of about 0.7 minutes, with an outlet temperature of 96.5° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.095 wt. %, based on the total weight of reactants.

Example 17

The reaction was conducted in the plug flow apparatus described above. A mixture of acetone to n-butyraldehyde (12.4 molar ratio) was fed at 150 ml/min, preheated to 106.6° C., and mixed with 0.15 ml/min of 50% caustic (0.019 molar ratio of caustic to n-butyraldehyde) prior to entering the reaction zone. The total amount of water present in the reaction mixture at the start of the reaction, based on the total weight of reactants, was thus about 0.095 wt. %. The reaction zone was sampled after the first reactor section to give a residence time of about 0.7 minutes, with an outlet temperature of 110.9° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.2 wt. %, based on the total weight of reactants.

Example 18

The reaction was conducted in the plug flow apparatus described above. A mixture of acetone to n-butyraldehyde (12.4 molar ratio) was fed at 150 ml/min, preheated to 60.2° C., and mixed with 0.30 ml/min of 50% caustic (0.038 molar ratio of caustic to n-butyraldehyde) prior to entering the reaction zone. The total amount of water present in the reaction mixture at the start of the reaction, based on the total weight of reactants, was thus about 0.19 wt. %. The reaction zone was sampled after the first reactor section to give a residence time of about 2.2 minutes, with an outlet temperature of 63.8° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.27 wt. %, based on the total weight of reactants.

Example 19

The reaction was conducted in the plug flow apparatus described above. A mixture of acetone to n-butyraldehyde (12.4 molar ratio) was fed at 150 ml/min, preheated to 106.5° C., and mixed with 0.30 ml/min of 50% caustic (0.038 molar ratio of caustic to n-butyraldehyde) prior to entering the reaction zone. The total amount of water present in the reaction mixture at the start of the reaction, based on the total weight of reactants, was thus about 0.19 wt. %. The reaction zone was sampled after the first reactor section to give a residence time of about 2.0 minutes, with an outlet temperature of 113.8° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.35 wt. %, based on the total weight of reactants.

Example 20

The reaction was conducted in the plug flow apparatus described above. A mixture of acetone to n-butyraldehyde (12.4 molar ratio) was fed at 150 ml/min, preheated to 106.5° C., and mixed with 0.6 ml/min of 25% caustic (0.038 molar ratio of caustic to n-butyraldehyde) prior to entering the reaction zone. The total amount of water present in the reaction mixture at the start of the reaction, based on the total weight of reactants, was thus about 0.57 wt. %. The reaction zone was sampled after the second reactor section to give a residence time of about 1.3 minutes, with an outlet temperature of 112° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 0.57 wt. %, based on the total weight of reactants.

Example 21

The reaction was conducted in the plug flow apparatus described above. A mixture of acetone to n-butyraldehyde (12.4 molar ratio) was fed at 150 ml/min, preheated to 105.5° C., and mixed with 1.2 ml/min of 25% caustic (0.076 molar ratio of caustic to n-butyraldehyde) prior to entering the reaction zone. The total amount of water present in the reaction mixture at the start of the reaction, based on the total weight of reactants, was thus about 1.1 wt. %. The reaction zone was sampled after the third reactor section to give a residence time of about 2.0 minutes, with an outlet temperature of 113.6° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 1.2 wt. %, based on the total weight of reactants.

Example 22

The reaction was conducted in the plug flow apparatus described above. A mixture of acetone to n-butyraldehyde (7.4 molar ratio) was fed at 150 ml/min, preheated to 105.5° C., and mixed with 1.2 ml/min of 25% caustic (0.048 molar ratio of caustic to n-butyraldehyde) prior to entering the reaction zone. The total amount of water present in the reaction mixture, based on the total weight of reactants, was thus about 1.1 wt. %. The reaction zone was sampled after the first reactor section to give a residence time of about 0.7 minutes, with an outlet temperature of 110.7° C. Selectivity and conversion data is summarized in Table 2. The calculated combined total amount of water in the reaction mixture at the end of the reaction, including both the amount of water provided at the start of the reaction, as well as the water of reaction created during the course of the reaction, was calculated to be 1.3 wt. %, based on the total weight of reactants.

Example 23 (Inventive) and Example 24 (Comparative)

A standard solution was prepared, consisting of 13.2 grams of 2-heptanone mixed with 1.99 grams of n-butyraldehyde. The molar ratio of 2-heptanone to n-butyraldehyde in the standard solution was 4.2. For Example 23 and Counterexample 24, the solution was then divided into approximately equal-sized portions and poured into two 4-dram capped vials. A teflon-coated stir bar was used for agitation, and each vial was placed on a magnetic stirring plate. Solutions of 50% and aqueous sodium hydroxide were prepared and added at time zero to each of the vials. The vials were sealed, stirred, and allowed to react initially at room temperature. The vials were sampled 80 minutes after introduction of the caustic catalyst. The samples were cooled to about 17° C. as collected and quenched by buffering to pH=7. All analyses were done by gas chromatography.

Example 23

7.05 grams of the standard solution were mixed with 0.20 grams of 50 weight percent NaOH and sealed. The molar ratio of 2-heptanone to n-butyraldehyde was 4.2. The molar ratio of sodium hydroxide to n-butyraldehyde was 0.19. The total amount of water present in the reaction mixture at the start of the reaction, based on the total weight of reactants, was thus about 1.4 wt. %. When sampled after 80 minutes reaction time, the conversion of n-butyraldehyde was complete. The solution did not separate into multiple liquid phases throughout the course of the experiment. The molar selectivity to the crossed ketone-aldehyde coupling products was 4-hydroxy-6-undecanone and 3-undecen-6-one was 94%, with 6% selectivity to the aldehyde self-condensation products 3-hydroxy-2-ethyl-hexanal and 2-ethyl-2-hexenal. The calculated combined total amount of water in the reaction mixture at the end of the reaction, including both the amount of water provided at the start of the reaction, as well as the water of reaction created during the course of the reaction, was calculated to be less than 4.2 wt. %, based on the total weight of reactants.

Example 24 (Comparative)

8.32 grams of the standard solution were mixed with 2.5 grams of 4.4 weight percent NaOH and sealed. The molar ratio of 2-heptanone to n-butyraldehyde was 4.2. The molar ratio of sodium hydroxide to n-butyraldehyde was 0.19. The total amount of water present in the reaction mixture at the start of the reaction, based on the total weight of reactants, was thus about 22.8 wt. Initially, the reaction mixture comprised two liquid phases and remained as such throughout the experiment. When sampled after 80 minutes reaction time, the conversion of n-butyraldehyde was about 90% complete. The molar selectivity to the crossed ketone-aldehyde coupling products was 4-hydroxy-6-undecanone and 3-undecen-6-one was 0.6%, with 99.4% selectivity to the aldehyde self-condensation products 3-hydroxy-2-ethyl-hexanal and 2-ethyl-2-hexenal. The calculated combined total amount of water in the reaction mixture at the end of the reaction, including both the amount of water provided at the start of the reaction, as well as the water of reaction created during the course of the reaction, was calculated to be 25 wt. %, based on the total weight of reactants.

Example 25

60.69 grams of acetone and 7.57 grams of 2-methyl-propanal were charged to a 200 ml 3-neck round bottom glass flask, fitted with a magnetic stirrer, nitrogen purge, electrically controlled heating mantle, and reflux condenser. The reactor was purged with nitrogen, and heated to reflux temperature, about 60° C., while maintaining stirring. Once a stable temperature had been reached 0.74 grams of 50 weight percent aqueous NaOH was injected into the reactor. These specifications gave a total feed of 10 moles of acetone per mole of 2-methyl-propanal and 0.088 moles caustic per mole of 2-methyl-propanal. The total amount of water present in the reaction mixture at the start of the reaction, based on the total weight of reactants, was thus about 0.53 wt. %. The reaction mixture was allowed to reflux for 50 minutes, at about 60° C. throughout the experiment. After 50 minutes of reaction time the reaction mixture was sampled. The sample was cooled to about 17° C. as collected, quenched by buffering to pH=7, and analyzed by gas chromatography. The conversion of 2-methyl-propanal was 97%. The molar selectivity of 2-methyl-propanal to various species were as follows: 4-hydroxy-5-methyl 2-hexanone, 37%;

5-methyl-3-hexen-2-one, 52%; C11 condensation products resulting from the further reaction of 5-methyl-3-hexen-2-one with 2-methyl-propanal, 10%. No 2-methyl-propanal self-condensation products were observed. The calculated combined total amount of water in the reaction mixture at the end of the reaction, including both the amount of water provided at the start of the reaction, as well as the water of reaction created during the course of the reaction, was calculated to be 1.91 wt. %, based on the total weight of reactants.

Example 26

6.60 grams of 2-pentanone was charged with 1.44 grams of n-butyraldehyde into a 6-dram capped vial. A teflon-coated stir bar was dropped in, and the vial was placed on a magnetic stirring plate. At time zero, 0.09 grams of 50 weight percent aqueous sodium hydroxide was added to the vials. These specifications gave a total feed of 4.6 moles of 2-pentanone per mole of n-butyraldehyde and 0.056 moles caustic per mole of n-butyraldehyde. The total amount of water present in the reaction mixture at the start of the reaction, based on the total weight of reactants, was thus about 0.6 wt. %. The vial was sealed, stirred, and allowed to react initially at room temperature. A sample was taken after fifteen minutes of reaction time. The sample was cooled, quenched by buffering to pH=7, and analyzed by gas chromatography. The conversion of n-butyraldehyde was 99%. The molar selectivity of n-butyraldehyde to various species were as follows: 4-hydroxy-6-nonanone, 65%; 4-nonen-6-one, 25%; n-butyraldehyde self-condensation products, 10%. The calculated combined total amount of water in the reaction mixture at the end of the reaction, including both the amount of water provided at the start of the reaction, as well as the water of reaction created during the course of the reaction, was calculated to be 1.9 wt. %, based on the total weight of reactants.

Example 27

59.9 grams of pinacolone and 12.0 grams of 4-chlorobenzaldehyde were charged to a 100 ml autoclave fitted with a magnetic stirrer, nitrogen purge, cooling coil, temperature-controlled band heater, and blow case for introduction of reactants and catalysts under pressure. The blow case was charged with 0.65 grams of 25% aqueous sodium hydroxide solution and valved off from the reactor vessel. These specifications gave a total feed of 7 moles of pinacolone per mole of 4-chlorobenzaldehyde and 0.047 moles caustic per mole of chlorobenzaldehyde. The total amount of water present in the reaction mixture at the start of the reaction, based on the total weight of reactants, was thus about 0.67 wt. %. The autoclave was sealed, purged with nitrogen, and heated to 160° C., while stirring at 1800 rpm. Once a stable temperature had been reached the blow case was pressurized with nitrogen and the valve was opened to allow introduction of the blow case contents into the reaction vessel. The contents of the reactor were maintained at 160° C. and sampled three minutes after introduction of the caustic. The sample was cooled as collected, neutralized with acetic acid, and analyzed by gas chromatography. Conversion of 4-chlorobenzaldehyde was 97.1% at 96% selectivity to 4,4-dimethyl-1-(p-chlorophenyl)-1-penten-3-one. The calculated combined total amount of water in the reaction mixture at the end of the reaction, including both the amount of water provided at the start of the reaction, as well as the water of reaction created during the course of the reaction, was calculated to be 2.6 wt. %, based on the total weight of reactants.

Example 28

59.9 grams of pinacolone and 12.0 grams of 4-chlorobenzaldehyde were charged to a 100 ml autoclave fitted with a magnetic stirrer, nitrogen purge, cooling coil, temperature-controlled band heater, and blow case for introduction of reactants and catalysts under pressure. The blow case was charged with 2.25 grams of 25% aqueous sodium hydroxide solution and valved-off from the reactor vessel. These specifications gave a total feed of 7 moles of pinacolone per mole of 4-chlorobenzaldehyde and 0.16 moles caustic per mole of chlorobenzaldehyde. The total amount of water present in the reaction mixture at the start of the reaction, based on the total weight of reactants, was thus about 2.3 wt. %. The autoclave was sealed, purged with nitrogen, and heated to 130° C., while stirring at 1800 rpm. Once a stable temperature had been reached the blow case was pressurized with nitrogen and the valve was opened to allow introduction of the blow case contents into the reaction vessel. The contents of the reactor were maintained at 130° C. and sampled fifteen minutes after introduction of the caustic. The sample was cooled as collected, neutralized with acetic acid, and analyzed by gas chromatography. Conversion of 4-chlorobenzaldehyde was 98.2% at 99.9% selectivity to 4,4-dimethyl-1-(p-chlorophenyl)-1-penten-3-one. The calculated combined total amount of water in the reaction mixture at the end of the reaction, including both the amount of water provided at the start of the reaction, as well as the water of reaction created during the course of the reaction, was calculated to be 4.2 wt. %, based on the total weight of reactants.

Example 29

The reaction was conducted in the plug flow apparatus described above for examples 10–22. A mixture of pinacolone to 4-chlorobenzaldehyde (7.0 molar ratio) was fed at 150 ml/min, preheated to 160° C., and mixed with 1.1 ml/min of 25% caustic (0.07 molar ratio of caustic to 4-chlorobenzaldehyde) prior to entering the reaction zone. The total amount of water present in the reaction mixture, based on the total weight of reactants, was thus about 0.99 wt. %. The reaction zone was sampled after the third reactor section to give a residence time of about 1.8 minutes, with an outlet temperature of 162° C. Conversion of 4-chlorobenzaldehyde was 95.4% at 96% selectivity to 4,4-dimethyl-1-(p-chlorophenyl)-1-penten-3-one. The calculated combined total amount of water in the reaction mixture at the end of the reaction, including both the amount of water provided at the start of the reaction, as well as the water of reaction created during the course of the reaction, was calculated to be 2.9 wt. %, based on the total weight of reactants.

Example 30

62.12 grams of acetone and 28.11 grams of 4-chlorobenzaldehyde were charged to a 100 ml autoclave fitted with a magnetic stirrer, nitrogen purge, cooling coil, temperature-controlled band heater, and blow case for introduction of reactants and catalysts under pressure. The blow case was charged with 0.65 grams of 25% aqueous sodium hydroxide solution and valved-off from the reactor vessel. These specifications gave a total feed of 5.3 moles of acetone per mole of 4-chlorobenzaldehyde and 0.02 moles caustic per mole of 4-chlorobenzaldehyde. The total amount of water present in the reaction mixture at the start of the reaction, based on the total weight of reactants, was thus about 0.53 wt. %. The autoclave was sealed, purged with nitrogen, and heated to 100° C., while stirring at 1800 rpm. Once a stable temperature had been reached the blow case was pressurized with nitrogen and the valve was opened to allow introduction of the blow case contents into the reaction vessel. The contents of the reactor were maintained at 100° C. and sampled three minutes after introduction of the caustic. The sample was cooled as collected, neutralized with acetic acid, and analyzed by gas chromatography. Conversion of 4-chlorobenzaldehyde was 99.7% at 95.7% selectivity to 1-(p-chlorophenyl)-1-buten-3-one. The calculated combined total amount of water in the reaction mixture at the end of the reaction, including both the amount of water provided at the start of the reaction, as well as the water of reaction created during the course of the reaction, was calculated to be 4.4 wt. %, based on the total weight of reactants.

Example 31

64.13 grams of acetone and 22.43 grams of cyclohexanecarboxaldehyde were charged to a 100 ml autoclave fitted with a magnetic stirrer, nitrogen purge, cooling coil, temperature-controlled band heater, and blow case for introduction of reactants and catalysts under pressure. The blow case was charged with 0.65 grams of 25% aqueous sodium hydroxide solution and valved-off from the reactor vessel. These specifications gave a total feed of 5.5 moles of acetone per mole of cyclohexanecarboxaldehyde and 0.0203 moles caustic per mole of cyclohexanecarboxaldehyde. The total amount of water present in the reaction mixture at the start of the reaction, based on the total weight of reactants, was thus about 0.56 wt. %. The autoclave was sealed, purged with nitrogen, and heated to 100° C., while stirring at 1800 rpm. Once a stable temperature had been reached the blow case was pressurized with nitrogen and the valve was opened to allow introduction of the blow case contents into the reaction vessel. The contents of the reactor were maintained at 100° C. and sampled three minutes and 15 minutes after introduction of the caustic. Samples were cooled as collected, neutralized with acetic acid, and analyzed by gas chromatography. At three minutes, conversion of cyclohexanecarboxaldehyde was 90% at molar selectivities of 68% and 28% to 1-cyclohexyl-1-buten-3-one and 1-hydroxy-1-cyclohexyl-3-butanone respectively. At 15 minutes, conversion of cyclohexanecarboxaldehyde was 97.2% at molar selectivities of 86% and 8% to 1-cyclohexyl-1-buten-3-one and 1-hydroxy-1-cyclohexyl-3-butanone respectively. The calculated combined total amount of water in the reaction mixture at the end of the reaction, including both the amount of water provided at the start of the reaction, as well as the water of reaction created during the course of the reaction, was calculated to be 1.7 wt. %, based on the total weight of reactants.

TABLE 1

Results for Examples 1–4

| Example | Temp, ° C. | Acetone to Butyraldehyde Molar Ratio | Caustic/ Butyraldehyde Molar Ratio | Time, min | % Conversion of Butyraldehyde | % Sel to 4H2H | % Sel to 3E2H | Total % Sel to 4H2H + 3E2H | % Sel to EHA |
|---|---|---|---|---|---|---|---|---|---|
| 1 | 80 | 13.1 | 0.08 | 2.8 | 50% | 92.3% | 7.7 | 100% | none |
|   |   |   |   | 5.0 | 96% | 55.6% | 37.1% | 92.7% | 2.0% |
| 2 | 90 | 13.4 | 0.37 | 1.6 | 50% | 86.0% | 9.3% | 95.3% | 1.4% |
|   |   |   |   | 5.7 | 96% | 14.9% | 69.4% | 84.3% | 1.5% |
| C-3 | 80 | 13.0 | 0.325 | 0.5 | 50% | 64.8% | 17.7% | 82.5% | 19.2% |
|   |   |   |   | 2.0 | 96% | 22.9% | 51.4% | 74.3% | 17.8% |
| C-4 | 60 | 14.8 | 2 weight % reactor loading | 6.5 | 50% | 68.0% | 16.7% | 84.7% | 15.2% |
|   |   |   |   | 95 | 94% | 13.8% | 43.3% | 57.1% | 6.2% |

Where:
4H2H = 4-hydroxy-2-heptanone
3E2H = 3-hepten-2-one
EHA = 2-ethyl-2-hexenal

TABLE 2

Results for Examples 10–22

| Example | % Conversion of Butyraldehyde | % Sel to 4H2H | % Sel to 3E2H | Total % Sel to 4H2H + 3E2H | % Sel to EHA |
|---|---|---|---|---|---|
| 10 | 96% | 81.8% | 7.4% | 89.2% | 2.8% |
| 11 | 25% | 92.9% | 7.1% | 100% | None |
| 12 | 98% | 81.1% | 8.8% | 89.9% | 3.7% |
| 13 | 6% | 100% | None | 100% | None |
| 14 | 22% | 91.5% | 8.5% | 100% | None |
| 15 | 95% | 93.0% | 2.1% | 95.1% | 2.9%. |
| 16 | 19% | 100% | None | 100% | None |
| 17 | 97% | 91.8% | 4.8% | 96.6% | 3.4% |
| 18 | 97% | 93.4% | 3.7% | 97.1% | 2.9% |
| 19 | 98% | 90.7% | 7.0% | 97.7% | 2.3% |
| 20 | 18% | 100% | None | 100% | None |
| 21 | 98% | 92.7% | 4.7% | 97.4% | None |
| 22 | 97% | 86.0% | 6.0% | 92.0% | 6.1% |

Where:
4H2H = 4-hydroxy-2-heptanone
3E2H = 3-hepten-2-one
EHA = 2-ethyl-2-hexenal For Examples 32 to 37 analyses were done by gas chromatography using a Hewlett-Packard model 5890 gas chromatograph, equipped with HP-1 column (50 meters×0.2 mm ID×0.5 micron film), FID detector, and auto injector. For each analysis, the initial temperature of the column was set at 60° C., held for 9 minutes, and ramped to 300° C. at a rate of 20° C./minute, and held for 10 minutes at 300° C.

Example 32

262 grams of methyl isobutyl ketone, 320 grams of 2-ethylhexanal, and 20 grams of 50% aqueous sodium hydroxide were charged to a 1000 mL three-neck round bottom flask. These specifications gave a total feed of 1.05 moles of methyl isobutyl ketone per mole of 2-ethylhexanal and 0.1 moles caustic per mole of 2-ethylhexanal. The total amount of water present in the reaction mixture at the start of the reaction, based on the total weight of reactants, was thus about 1.66 wt. %. The reaction mixture was heated to 100° C. and stirred for 60 minutes. After the reaction was complete, the mixture was allowed to cool. The reactor effluent was sampled to determine percent conversion of 2-ethylhexanal and selectivity to 7-ethyl-2-methylundec-5-en-4-one. A summary of reaction conditions and results is given in Table 3. The calculated combined total amount of water in the reaction mixture at the end of the reaction, including both the amount of water provided at the start of the reaction, as well as the water of reaction created during the course of the reaction, was calculated to be less than 6 wt. %, based on the total weight of reactants.

Example 33

262 grams of methyl isobutyl ketone, 320 grams of 2-ethylhexanal, and 20 grams of 50% aqueous sodium hydroxide were charged to a 1000 mL three-neck round bottom flask, fitted with a Dean-Stark trap. These specifications gave a total feed of 1.05 moles of methyl isobutyl ketone per mole of 2-ethylhexanal and 0.1 moles caustic per mole of 2-ethylhexanal. The total amount of water present in the reaction mixture at the start of the reaction, based on the total weight of reactants, was thus about 1.66 wt. %. The reaction mixture was heated to 100° C. and water was removed from the reaction zone by distillation of the heterogeneous water-MIBK azeotrope, condensation of the evolved vapors, and collection of the two phase mixture in the Dean-Stark trap. The upper MIBK-rich organic layer was automatically returned to the reaction zone via the trap overflow mechanism. The reaction was then held at 100° C. stirred for 60 minutes. After the reaction was complete, the mixture was allowed to cool. Upon cooling the reactor effluent separated into two layers. The organic layer was sampled to determine percent conversion of 2-ethylhexanal and selectivity to 7-ethyl-2-methylundec-5-en-4-one. The lower, water-rich layer was removed from the Dean-Stark trap and found to contain about 18 grams of water. This corresponds to removal of about 49% of the theoretical water of reaction. A summary of reaction conditions and results is given in Table 3. The calculated combined total amount of water in the reaction mixture at the end of the reaction, including both the amount of water provided at the start of the reaction, as well as the water of reaction created during the course of the reaction, was calculated to be 4.7 wt. %, based on the total weight of reactants.

Example 34

151 grams of methyl isobutyl ketone, 96 grams of 2-ethylhexanal, and 6 grams of 50% aqueous sodium hydroxide were charged to a 300 mL autoclave. These specifications gave a total feed of 2.00 moles of methyl isobutyl ketone per mole of 2-ethylhexanal and 0.1 moles caustic per mole of 2-ethylhexanal. The total amount of water present in the reaction mixture at the start of the reaction, based on the total weight of reactants, was thus about 1.18 wt. %. The autoclave was sealed and the reaction mixture was heated to 120° C. under 100-psi nitrogen and stirred for 120 minutes. After the reaction was complete, the mixture was allowed to cool. The reactor effluent was sampled to determine percent conversion of 2-ethylhexanal and selectivity to 7-ethyl-2-methylundec-5-en-4-one. A summary of reaction conditions and results is given in Table 3. The calculated combined total amount of water in the reaction mixture at the end of the reaction, including both the amount of water provided at the start of the reaction, as well as the water of reaction created during the course of the reaction, was calculated to be less than 6 wt. %, based on the total weight of reactants.

Example 35 (Comparative)

262 grams of methyl isobutyl ketone, 320 grams of 2-ethylhexanal, and 100 grams of 50% aqueous sodium hydroxide were charged to a 1000 mL three-neck round bottom flask. These specifications gave a total feed of 1.05 moles of methyl isobutyl ketone per mole of 2-ethylhexanal and 0.5 moles caustic per mole of 2-ethylhexanal. The total amount of water present in the reaction mixture at the start of the reaction, based on the total weight of reactants, was thus about 7.31 wt. %. The reaction mixture was heated to 100° C. and stirred for 60 minutes. After the reaction was complete, the mixture was allowed to cool. The organic layer was sampled to determine percent conversion of 2-ethylhexanal and selectivity to 7-ethyl-2-methylundec-5-en-4-one. A summary of reaction conditions and results is given in Table 3. The calculated combined total amount of water in the reaction mixture at the end of the reaction, including both the amount of water provided at the start of the reaction, as well as the water of reaction created during the course of the reaction, was calculated to be 12.9 wt. %, based on the total weight of reactants.

Example 36 (Comparative)

105 grams of methyl isobutyl ketone, 128 grams of 2-ethylhexanal, and 133 grams of 3% aqueous sodium hydroxide were charged to a 1000 mL three-neck round bottom flask. These specifications gave a total feed of 1.05 moles of methyl isobutyl ketone per mole of 2-ethylhexanal and 0.1 moles caustic per mole of 2-ethylhexanal. The total amount of water present in the reaction mixture at the start of the reaction, based on the total weight of reactants, was thus about 35.2 wt. %. The reaction mixture was heated to 100° C. and stirred for 60 minutes. After the reaction was complete, the mixture was allowed to cool. The organic layer was sampled to determine percent conversion of 2-ethylhexanal and selectivity to 7-ethyl-2-methylundec-5-en-4-one. A summary of reaction conditions and results is given in Table 3. The calculated combined total amount of water in the reaction mixture at the end of the reaction, including both the amount of water provided at the start of the reaction, as well as the water of reaction created during the course of the reaction, was calculated to be 35.7 wt. %, based on the total weight of reactants.

Example 37 (Comparative)

262 grams of methyl isobutyl ketone, 320 grams of 2-ethylhexanal, and 20 grams of 50% aqueous sodium hydroxide were charged to a 1000 mL three-neck round bottom flask, fitted with a Dean-Stark trap. These specifications gave a total feed of 1.05 moles of methyl isobutyl ketone per mole of 2-ethylhexanal and 0.1 moles caustic per mole of 2-ethylhexanal. The total amount of water present in the reaction mixture at the start of the reaction, based on the total weight of reactants, was thus about 1.66 wt. %. The reaction mixture was heated to 120° C., and water was removed from the reaction zone by distillation of the heterogeneous water-MIBK azeotrope, condensation of the evolved vapors, and collection of the two-phase mixture in the Dean-Stark trap. The upper MIBK-rich organic layer was automatically returned to the reaction zone via the trap overflow mechanism. After the reaction was complete, the mixture was allowed to cool. Upon cooling, the reactor effluent separated into two layers. The organic layer was sampled to determine percent conversion of 2-ethylhexanal and selectivity to 7-ethyl-2-methylundec-5-en-4-one. The total amount of water in the reaction mixture at the end of the reaction was measured and found to be 1.86 wt. %, based on the total weight of reactants. The lower water-rich layer was removed from the Dean-Stark trap and found to contain about 32 grams of water. This corresponds to removal of about 96% of the theoretical water of reaction. A summary of reaction conditions and results is given in Table 3.

to 2,8-dimethyl-3-hydroxy-5-nonanone, a combined selectivity of 91% to C11 ketone materials. The lower, water-rich layer was removed from the Dean-Stark trap and found to contain about 14 grams of water. This corresponds to removal of about 70% of the theoretical water of reaction. Initially, the water concentration was about 0.88 wt % in the reaction vessel and the water concentration was 2.5% at the end of the reaction.

Example 39 (Comparative)

161.1 grams of 5-methyl-2-hexanone and 8.38 grams of 50% aqueous sodium hydroxide were charged to a 500 mL three-neck round bottom flask, fitted with a Dean-Stark trap. The vessel was heated to 60° C., and a mixture of 108.1 grams of 5-methyl-2-hexanone and 90.4 grams of 2-methyl-propanal was added dropwise over 180 minutes. These specifications gave a total feed of 1.88 moles of 5-methyl-2-hexanone per mole of 2-methyl-propanal, and 0.083 moles caustic per mole of 2-methyl-propanal. The reaction was held for an additional two hours at 70° C. The reaction mixture was sampled and conversion and selectivity were calculated from the analytical data. The conversion of 3-methyl-propanal was about 98%, with a selectivity of 30% to 2,8-dimethyinon-3-en-5-one and 70% to 2,8-dimethyl-3-hydroxy-5-nonanone. The reaction mixture was heated to

TABLE 3

Conditions and Results for Examples 32–37

| Ex. | Temp | Ald. | Ket. | % Caustic | Amt. H2O (g) | Amt. NaOH (Caustic) (g) | Ketone/ Aldehyde (moles) | Caustic/ Aldehyde (moles) | Time min. | Conv. | Selectivity |
| --- | --- | --- | --- | --- | --- | --- | --- | --- | --- | --- | --- |
| 32 | 100 | EHA | MIBK | 50 | 10 | 10 | 1.05 | 0.1 | 60 | 60.58 | 97.92 |
| 33 | 100 | EHA | MIBK | 50 | 10 | 10 | 1.05 | 0.1 | 60 | 83.33 | 97.95 |
| 34 | 120 | EHA | MIBK | 50 | 3 | 3 | 2 | 0.1 | 120 | 90.26 | 98.34 |
| C35 | 100 | EHA | MIBK | 50 | 50 | 50 | 1.05 | 0.5 | 60 | 91.55 | 92.79 |
| C36 | 100 | EHA | MIBK | 3 | 129 | 3 | 1.05 | 0.1 | 60 | 0.97 | 26.76 |
| C37 | 120 | EHA | MIBK | 50 | 10 | 10 | 1.05 | 0.1 | 60 | 89.08 | 83.85 |

MIBK = 4-methylpentan-2-one
EHA = 2-ethyl-2-hexenal

Example 38

169.6 grams of 5-methyl-2-hexanone and 6.46 grams of 50% aqueous sodium hydroxide were charged to a 500 mL three-neck round bottom flask, fitted with a Dean-Stark trap. The vessel was heated to 60° C., and a mixture of 91.7 grams of 5-methyl-2-hexanone and 100.3 grams of 2-methyl-propanal was added dropwise over 150 minutes. These specifications gave a total feed of 1.64 moles of 5-methyl-2-hexanone per mole of 2-methyl-propanal and 0.057 moles caustic per mole of 2-methyl-propanal. The total amount of water present in the reaction mixture at the start of the reaction, based on the total weight of reactants, was thus about 0.88 wt. %. The reaction mixture was heated to the boiling point, and water was removed from the reaction zone by distillation of the heterogeneous water-reactant azeotropes, condensation of the evolved vapors, and collection of the two-phase mixture in the Dean-Stark trap. The upper, organic-rich layer was automatically returned to the reaction zone via the trap overflow mechanism. After the reaction was complete, the mixture was allowed to cool. Upon cooling, the reactor effluent separated into two layers. The organic layer was sampled and analyzed by GC. The conversion of 3-methyl-propanal was about 98%, with a selectivity of 73% to 2,8-dimethylnon-3-en-5-one and 18% the boiling point and water was removed from the reaction zone by distillation of the heterogeneous water-reactant azeotropes, condensation of the evolved vapors, and collection of the two-phase mixture in the Dean-Stark trap. The upper, organic-rich layer was automatically returned to the reaction zone via the trap overflow mechanism. After 23.5 grams of water had collected in the Dean-Stark trap, the mixture was allowed to cool. This corresponds to removal of about 100.4% of the theoretical water of reaction, assuming complete conversion of 3-methyl-pentanal to 2,8-dimethylnon-3-en-5-one. The reactor effluent was sampled and analyzed by GC. The 3-methyl-propanal was completely reacted, with a selectivity of about 15% to 2,8-dimethyinon-3-en-5-one and no 2,8-dimethyl-3-hydroxy-5-nonanone. Initially, the water concentration was about 1.1 wt % in the reaction vessel, and the water concentration was less than 0.8% at the end of the reaction.

The invention has been described in detail with particular reference to preferred embodiments thereof, but it will be understood that variations and modifications can be effected within the spirit and scope of the invention. In the specification, there have been disclosed typical preferred embodiments of the invention and, although specific terms are employed, they are used in a generic and descriptive sense only, and not for purposes of limitation, the scope of the invention being set forth in the following claims.

We claim:

1. A process for producing one or more of a β-hydroxyketone product or an α,β-unsaturated ketone product, the process comprising reacting an aldehyde reactant with a ketone reactant, the ketone reactant having at least one hydrogen atom alpha to the carbonyl, in a reaction mixture comprising the aldehyde reactant, the ketone reactant, and a catalyst comprised of a hydroxide or alkoxide of an alkali metal or an alkaline earth metal, wherein the hydroxide or alkoxide is provided in a solution having a concentration of at least 15 wt. %, or as a solid,
   wherein no more than 6 wt. % water, based on the total of the water provided and water generated by reaction, is present in the reaction mixture, with respect to the total weight of the reaction mixture, and
   wherein the reacting is carried out at a reaction time of no more than 120 minutes.

2. The process according to claim 1, wherein no more than 4 wt. % water is present in the reaction mixture, with respect to the total weight of the reaction mixture.

3. The process according to claim 1, wherein no more than 3 wt. % water is present in the reaction mixture, with respect to the total weight of the reaction mixture.

4. The process according to claim 1, wherein the catalyst is provided as a solution of a hydroxide or alkoxide of an alkali metal or an alkaline earth metal, wherein the hydroxide or alkoxide is provided in the solution at a concentration of at least 20 wt. %.

5. The process according to claim 1, wherein the catalyst is provided as a solution of a hydroxide or alkoxide of an alkali metal or an alkaline earth metal, wherein the hydroxide or alkoxide is provided in the solution at a concentration of at least 25 wt. %.

6. The process according to claim 1, wherein the catalyst is provided as a solution of a hydroxide or alkoxide of an alkali metal or an alkaline earth metal, wherein the hydroxide or alkoxide is provided in the solution at a concentration of at least 50 wt. %.

7. The process according to claim 1, wherein the reaction time is no more than 60 minutes.

8. The process according to claim 1, wherein the reaction time is no more than 30 minutes.

9. The process according to claim 1 wherein the reaction time is no more than 20 minutes.

10. The process according to claim 1, wherein the reaction time is no more than 10 minutes.

11. The process according to claim 1, wherein the reacting is carried out in the substantial absence of a solubilizing agent.

12. The process according to claim 1, wherein the molar ratio of ketone reactant to aldehyde reactant is from 1:1 to 20:1.

13. The process according to claim 1, wherein the molar ratio of ketone reactant to aldehyde reactant is from 1:1 to 14:1.

14. The process according to claim 1, wherein from 1.05 to 10 moles of ketone reactant are used per mole of aldehyde.

15. The process according to claim 1, wherein the molar ratio of the hydroxide or alkoxide of the alkali metal or alkaline earth metal catalyst to the aldehyde reactant is from 0.001:1 to 0.45:1.

16. The process according to claim 1, wherein the molar ratio of the hydroxide or alkoxide of an alkali metal or alkaline earth metal catalyst to the aldehyde reactant is from 0.005:1 to 0.45:1.

17. The process according to claim 1, wherein the molar ratio of the hydroxide or alkoxide of the alkali metal or alkaline earth metal catalyst to the aldehyde reactant is from 0.001:1 to 0.25:1.

18. The process according to claim 1, wherein the molar ratio of the hydroxide or alkoxide of the alkali metal or alkaline earth metal catalyst to the aldehyde reactant is from 0.005:1 to 0.15:1.

19. The process according to claim 1, wherein the molar ratio of the hydroxide or alkoxide of the alkali metal or alkaline earth metal catalyst to the aldehyde reactant is from 0.005:1 to 0.10:1.

20. The process according to claim 1, wherein the hydroxide or alkoxide of the alkali metal or alkaline earth metal comprises one or more of: sodium hydroxide, potassium hydroxide, cesium hydroxide, lithium hydroxide, magnesium hydroxide, calcium hydroxide, barium hydroxide, sodium methoxide, sodium ethoxide, sodium propoxide, sodium butoxide, potassium methoxide, potassium ethoxide, potassium propoxide, potassium butoxide, cesium methoxide, cesium ethoxide, cesium propoxide, cesium butoxide, lithium methoxide, lithium ethoxide, lithium propoxide, lithium butoxide, magnesium methoxide, magnesium ethoxide, magnesium propoxide, magnesium butoxide, calcium methoxide, calcium ethoxide, calcium propoxide, calcium butoxide, barium methoxide, barium ethoxide, barium propoxide, or barium butoxide.

21. The process according to claim 1, wherein the hydroxide or alkoxide of the alkali metal or alkaline earth metal comprises one or more of: sodium hydroxide or potassium hydroxide.

22. The process according to claim 1, wherein the reacting is carried out at a temperature from 25° C. to 175° C.

23. The process according to claim 1, wherein the reacting is carried out at a temperature from 40° C. to 165° C.

24. The process according to claim 1, wherein the catalyst is provided as an oxide of an alkali metal or an alkaline earth metal which forms in the reaction mixture a hydroxide.

25. The process according to claim 1, wherein the reacting is carried out batchwise.

26. The process according to claim 1, wherein the reacting is carried out in a continuous plug flow reactor.

27. The process according to claim 1, wherein the reacting is carried out in a series of two or more continuous stirred tank reactors.

28. The process according to claim 1, wherein the aldehyde reactant comprises one or more of: acetaldehyde; propionaldehyde; n-butyraldehyde; 2-methyl-propanal; n-pentanal; 2-methyl-butanal; 3-methyl-butanal; 2,2-dimethyl-propanal; n-hexanal; 2-ethyl-butanal; 2,2-dimethylbutanal; 2,3-dimethylbutanal; 2-methyl-pentanal; 3-methylpentanal; 4-methyl-pentanal; n-heptanal; 2-methylhexanal; 2-ethylpentanal; 2,2-dimethylpentanal; 2,3-dimethylpentanal; 2,4-dimethylpentanal; 2-ethyl-3-methylbutanal; 2-ethyl-2-methylbutanal; n-octanal; 2-ethylhexanal; n-nonanal; n-decanal; n-undecanal; n-dodecanal; benzaldehyde; 4-chlorobenzaldehyde; 3-chlorobenzaldehyde; 2-chlorobenzaldehyde; phenyl acetaldehyde; o-tolualdehyde; m-tolualdehyde; p-tolualdehyde; p-methoxybenzaldehyde; o-ethoxybenzaldehyde; m-methoxybenzaldehyde; cyclopropane carboxaldehyde; cyclobutane carboxaldehyde; cyclopentane carboxaldehyde; cyclohexane carboxaldehyde; 2-methylcyclohexane carboxaldehyde; 3-methylhexane carboxaldehyde; or 4-methylhexane carboxaldehyde.

29. The process according to claim 1, wherein the ketone reactant comprises one or more of: acetone, 2-butanone, 2-pentanone, 3-methyl-2-butanone, 2-hexanone, 4-methyl-2-pentanone, pinacolone, 2-heptanone, 5-methyl-2- hexanone, 2-octanone, 2-nonanone, 2-decanone, 2-undecanone, 2-dodecanone, cyclobutanone, cyclopentanone, cyclohexanone, cyclooctanone, 3,3-5-trimethylcyclohexanone, tricyclo[5.2.1.02,6]decan-8-one, or acetophenone.

30. The process according to claim 1, wherein the reacting is carried out at a temperature from 50° C. to 160° C.

31. The process according to claim 1, wherein the reacting is carried out at a pressure from about 1 to about 70 atmospheres.

32. The process according to claim 1, wherein the reacting is carried out at a pressure from about 1 to about 45 atmospheres.

33. The process according to claim 1, wherein a portion of the water of reaction created during the reaction is removed during the course of the reaction.

34. The process according to claim 33, wherein the portion of the water of reaction removed is no more than 80% of the theoretical amount of water generated.

35. The process according to claim 1, wherein the reacting is carried out in one or more of: a tubular reactor operated adiabatically, a staged tubular reactor with interstage heat exchange; a staged tubular reactor with interstage cold-shotting of reactant; an annular temperature-controlled jacketed tubular reactor; or a shell-and-tube heat exchanger.

36. The process according to claim 35, wherein the reaction time is no more than 10 minutes.

37. The process according to claim 35, wherein the reaction time is no more than 2 minutes.

38. A process for producing one or more of: 7-ethyl-2-methylundec-5-en-4-one or 6-hydroxy-7-ethyl-2methyl-undecan-4-one, the process comprising reacting 2-ethylhexanal with 4-methylpentan-2-one in the presence of a catalyst comprising a hydroxide or alkoxide of an alkali metal or an alkaline earth metal, wherein the hydroxide or alkoxide is provided in a solution having a concentration of at least 15 wt. %, or as a solid, wherein no more than 6 wt. % water, based on the total of the water provided and water generated by reaction, is present in the reaction mixture, with respect to the total weight of the reaction mixture, and wherein the reaction is carried out at a reaction time of no more than 120 minutes.

39. The process according to claim 38, wherein no more than 3 wt. % water is present in the reaction mixture, with respect to the total weight of the reaction mixture.

40. The process according to claim 38, wherein the catalyst is provided as a solution of a hydroxide or alkoxide of an alkali metal or an alkaline earth metal, wherein the hydroxide or alkoxide is provided in the solution at a concentration of at least 25 wt. %.

41. The process according to claim 38, wherein from 1.05 to 10 moles of ketone reactant are used per mole of aldehyde.

42. The process according to claim 38, wherein the molar ratio of the hydroxide or alkoxide of an alkali metal or alkaline earth metal catalyst to the aldehyde reactant is from 0.005:1 to 0.15:1.

43. The process according to claim 38, wherein the hydroxide or alkoxide of the alkali metal or alkaline earth metal comprises one or more of: sodium hydroxide or potassium hydroxide.

44. The process according to claim 38, wherein the reacting is carried out batchwise.

45. The process according to claim 38, wherein a portion of the water of reaction created during the reaction is removed during the course of the reacting.

46. The process according to claim 38, wherein the portion of the water of reaction removed is no more than 80% of the theoretical amount of water generated.

47. The process according to claim 38, wherein the reacting is carried out in one or more of: a tubular reactor operated adiabatically, astaged tubular reactor with interstage heat exchange; a staged tubular reactor with interstage cold-shotting of reactant; an annular temperature-controlled jacketed tubular reactor; or a shell-and-tube heat exchanger.

48. The process according to claim 47, wherein the reaction time is no more than 10 minutes.

49. A process for producing one or more of: 4-hydroxy-2-heptanone or 3-hepten-2-one, the process comprising reacting n-butyraldehyde with acetone in the presence of a catalyst comprising a hydroxide or alkoxide of an alkali metal or an alkaline earth metal, wherein the hydroxide or alkoxide is provided in a solution having a concentration of at least 15 wt. %, or as a solid, wherein no more than 6 wt. % water, based on the total of the water provided and water generated by reaction, is present in the reaction mixture, with respect to the total weight of the reaction mixture, and wherein the reaction is carried out at a reaction time of no more than 120 minutes.

50. The process according to claim 49, wherein no more than 4 wt. % water is present in the reaction mixture, with respect to the total weight of the reaction mixture.

51. The process according to claim 49, wherein the catalyst is provided as a solution of a hydroxide or alkoxide of an alkali metal or an alkaline earth metal, and wherein the hydroxide or alkoxide is provided in the solution at a concentration of at least 25 wt. %.

52. The process according to claim 49, wherein from 1.05 to 14 moles of ketone reactant are used per mole of aldehyde.

53. The process according to claim 49, wherein the molar ratio of the hydroxide or alkoxide of an alkali metal or alkaline earth metal catalyst to the aldehyde reactant is from 0.005:1 to 0.15:1.

54. The process according to claim 49, wherein the hydroxide or alkoxide of the alkali metal or alkaline earth metal comprises one or more of: sodium hydroxide or potassium hydroxide.

55. The process according to claim 49, wherein the reacting is carried out batchwise.

56. The process according to claim 49, wherein the reacting is carried out in a series of two or more continuous stirred tank reactors.

57. The process according to claim 49, wherein the reacting is carried out in one or more of: a tubular reactor operated adiabatically; a staged tubular reactor with interstage heat exchange; a staged tubular reactor with interstage cold-shotting of reactant; an annular temperature-controlled jacketed tubular reactor; or a shelf-and-tube heat exchanger.

58. The process according to claim 57, wherein the reaction time is no more than 10 minutes.

59. A process for producing one or more of: 4-hydroxy-5-methyl 2-hexanone or 5-methyl-3-hexen-2-one, the process comprising reacting 3-methyl-propanal with acetone in the presence of a catalyst comprising a hydroxide or alkoxide of an alkali metal or an alkaline earth metal, wherein the hydroxide or alkoxide is provided in a solution having a concentration of at least 15 wt. %, or as a solid, wherein no more than 6 wt. % water, based on the total of the water provided and water generated by reaction, is present in the reaction mixture, with respect to the total weight of the reaction mixture, and wherein the reaction is carried out at a reaction time of no more than 120 minutes.

60. The process according to claim 59, wherein no more than 4 wt. % water is present in the reaction mixture, with respect to the total weight of the reaction mixture.

61. The process according to claim 59, wherein the catalyst is provided as a solution of a hydroxide or alkoxide of an alkali metal or an alkaline earth metal, wherein the hydroxide or alkoxide is provided in the solution at a concentration of at least 25 wt. %.

62. The process according to claim 59, wherein from 1.05 to 14 moles of ketone reactant are used per mole of aldehyde.

63. The process according to claim 59, wherein the molar ratio of the hydroxide or alkoxide of an alkali metal or alkaline earth metal catalyst to the aldehyde reactant is from 0.005:1 to 0.15:1.

64. The process according to claim 59, wherein the hydroxide or alkoxide of the alkali metal or alkaline earth metal comprises one or more of: sodium hydroxide or potassium hydroxide.

65. The process according to claim 59, wherein the reacting is carried out batchwise.

66. The process according to claim 59, wherein the reacting is carried out in a series of two or more continuous stirred tank reactors.

67. The process according to claim 59, wherein the reacting is carried out in one or more of: a tubular reactor operated adiabatically; a staged tubular reactor with interstage heat exchange; a staged tubular reactor with interstage cold-shotting of reactant; an annular temperature-controlled jacketed tubular reactor; or a shell-and-tube heat exchanger.

68. The process according to claim 67, wherein the reaction time is no more than 10 minutes.

69. A process for producing one or more of: 3-hydroxy-2-pentanone or 3-penten-2-one, the process comprising reacting acetaldehyde with acetone in the presence of a catalyst comprising a hydroxide or alkoxide of an alkali metal or an alkaline earth metal, wherein the hydroxide or alkoxide is provided in a solution having a concentration of at least 15 wt. %, or as a solid,
wherein no more than 6 wt. % water, based on the total of the water provided and water generated by reaction, is present in the reaction mixture, with respect to the total weight of the reaction mixture, and
wherein the reaction is carried out at a reaction time of no more than 120 minutes.

70. The process according to claim 69, wherein no more than 3 wt. % water is present in the reaction mixture, with respect to the total weight of the reaction mixture.

71. The process according to claim 69, wherein the catalyst is provided as a solution of a hydroxide or alkoxide of an alkali metal or an alkaline earth metal, wherein the hydroxide or alkoxide is provided in the solution at a concentration of at least 25 wt. %.

72. The process according to claim 69, wherein from 1.05 to 14 moles of ketone reactant are used per mole of aldehyde.

73. The process according to claim 69, wherein the molar ratio of the hydroxide or alkoxide of an alkali metal or alkaline earth metal catalyst to the aldehyde reactant is from 0.005:1 to 0.15:1.

74. The process according to claim 69, wherein the hydroxide or alkoxide of the alkali metal or alkaline earth metal comprises one or more of: sodium hydroxide or potassium hydroxide.

75. The process according to claim 69, wherein the reaction is carried out batchwise.

76. The process according to claim 69, wherein the reaction is carried out in a series of two or more continuous stirred tank reactors.

77. The process according to claim 69, wherein the reaction is carried out in one or more of: a tubular reactor operated adiabatically; a staged tubular reactor with interstage heat exchange; a staged tubular reactor with interstage cold-shotting of reactant; an annular temperature-controlled jacketed tubular reactor; or a shell-and-tube heat exchanger.

78. The process according to claim 77, wherein the reaction time is no more than 10 minutes.

79. A process for producing one or more of: 6-methyl-3-hepten-2-one or 6-methyl-3-hydroxy-2-heptanone, the process comprising reacting acetone with 3-methyl-butanal in the presence of a catalyst comprising a hydroxide or alkoxide of an alkali metal or an alkaline earth metal, wherein the hydroxide or alkoxide is provided in a solution having a concentration of at least 15 wt. %, or as a solid,
wherein no more than 6 wt. % water, based on the total of the water provided and water generated by reaction, is present in the reaction mixture, with respect to the total weight of the reaction mixture, and
wherein the reaction is carried out at a reaction time of no more than 120 minutes.

80. The process according to claim 79, wherein no more than 4 wt. % water is present in the reaction mixture, with respect to the total weight of the reaction mixture.

81. The process according to claim 79, wherein the catalyst is provided as a solution of a hydroxide or alkoxide of an alkali metal or an alkaline earth metal, wherein the hydroxide or alkoxide is provided in the solution at a concentration of at least 25 wt. %.

82. The process according to claim 79, wherein from 1.05 to 14 moles of ketone reactant are used per mole of aldehyde.

83. The process according to claim 79, wherein the molar ratio of the hydroxide or alkoxide of an alkali metal or alkaline earth metal catalyst to the aldehyde reactant is from 0.005:1 to 0.15:1.

84. The process according to claim 79, wherein the hydroxide or alkoxide of the alkali metal or alkaline earth metal comprises one or more of: sodium hydroxide or potassium hydroxide.

85. The process according to claim 79, wherein the reaction is carried out batchwise.

86. The process according to claim 79, wherein the reaction is carried out in a series of two or more continuous stirred tank reactors.

87. The process according to claim 79, wherein the reaction is carried out in one or more of: a tubular reactor operated adiabatically; a staged tubular reactor with interstage heat exchange; a staged tubular reactor with interstage cold-shotting of reactant; an annular temperature-controlled jacketed tubular reactor; or a shell-and-tube heat exchanger.

88. The process according to claim 87, wherein the reaction time is no more than 10 minutes.

89. A process for producing one or more of: 4-hydroxy-undecan-6-one or 4-undecen-6-one, the process comprising reacting n-butanal with 2-heptanone in the presence of a catalyst comprising a hydroxide or alkoxide of an alkali metal or an alkaline earth metal, wherein the hydroxide or alkoxide is provided in a solution having a concentration of at least 15 wt. %, or as a solid,
wherein no more than 6 wt. % water, based on the total of the water provided and water generated by reaction, is present in the reaction mixture, with respect to the total weight of the reaction mixture, and wherein the reaction is carried out at a reaction time of no more than 120 minutes.

90. A process for producing one or more of: 2,8-dimethyl-3-hydroxy-nonan-5-one or 2,8-dimethyl-3-nonen-5-one, the process comprising reacting 2-methyl-propanal with 5-methyl-hexan-2-one in the presence of a catalyst comprising a hydroxide or alkoxide of an alkali metal or an alkaline earth metal, wherein the hydroxide or alkoxide is provided in a solution having a concentration of at least 15 wt. %, or as a solid, wherein no more than 6 wt. % water, based on the total of the water provided and water generated by reaction, is present in the reaction mixture, with respect to the total weight of the reaction mixture, and wherein the reaction is carried out at a reaction time of no more than 120 minutes.

91. A process for producing one or more of: 5-ethyl-4-hydroxy-nonan-2-one or 5-ethyl-3-nonen-2-one, the process comprising reacting 2-ethylhexanal with acetone in the presence of a catalyst comprising a hydroxide or alkoxide of an alkali metal or an alkaline earth metal, wherein the hydroxide or alkoxide is provided in a solution having a concentration of at least 15 wt. %, or as a solid, wherein no more than 6 wt. % water, based on the total of the water provided and water generated by reaction, is present in the reaction mixture, with respect to the total weight of the reaction mixture, and wherein the reaction is carried out at a reaction time of no more than 120 minutes.

92. A process for preparing one or more of a compound of the formulas:

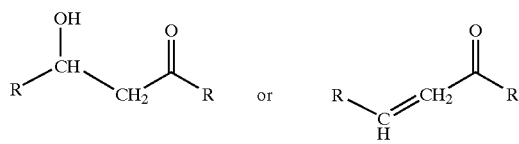

wherein each R is independently a hydrocarbyl group;

which process comprises contacting in a reaction mixture a compound of the formula

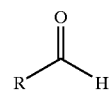

(i)

with a compound of the formula

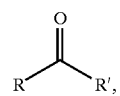

(ii)

wherein each R is independently a hydrocarbyl group and R' is a hydrocarbyl group having at least one hydrogen atom on the carbon atom which serves as the point of attachment, in the presence of (iii) a catalyst comprised of a hydroxide or $C_1$–$C_8$ alkoxide of an alkali metal or alkaline earth metal, wherein the hydroxide or $C_1$–$C_8$ alkoxide of an alkali metal or alkaline earth metal is provided by at least one of:

(a) in a solution having a concentration of at least 15 weight percent, or (b) as a solid, wherein no more than 6 weight percent water, based on the total weight of the water provided in the reaction mixture or the combination of water provided and water generated in situ is present in the reaction mixture upon completion, with respect to the total weight of the reaction mixture, and wherein the reaction is carried out within a period of no more than 120 minutes.

* * * * *